United States Patent
Ghiso et al.

(12) 
(10) Patent No.: US 6,670,195 B1
(45) Date of Patent: Dec. 30, 2003

(54) MUTANT GENES IN FAMILIAL BRITISH DEMENTIA AND FAMILIAL DANISH DEMENTIA

(75) Inventors: Jorge Ghiso, Elmhurst, NY (US); Ruben Vidal, Great Neck, NY (US); Blas Frangione, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/579,012

(22) Filed: May 26, 2000

Related U.S. Application Data

(60) Provisional application No. 60/136,238, filed on May 26, 1999.

(51) Int. Cl.$^7$ .......................... C07K 16/00; C12P 21/08; G01N 33/563
(52) U.S. Cl. ................. 436/513; 530/387.1; 530/387.9; 530/388.1
(58) Field of Search ............................ 530/387.1, 388.1

(56) References Cited

U.S. PATENT DOCUMENTS

| | | | |
|---|---|---|---|
| 5,387,742 A | 2/1995 | Cordell ........................ | 800/12 |
| 5,612,486 A | 3/1997 | McConlogue et al. ........ | 800/12 |
| 5,720,936 A | 2/1998 | Wadsworth et al. .......... | 424/9.1 |
| 5,811,633 A | 9/1998 | Wadsworth et al. .......... | 800/12 |
| 5,837,672 A | 11/1998 | Schenk et al. ................. | 514/2 |
| 5,849,999 A | 12/1998 | Neve et al. .................... | 800/3 |
| 5,851,787 A | 12/1998 | Wasco et al. ............... | 435/69.1 |
| 5,877,399 A | 3/1999 | Hsiao et al. .................... | 800/3 |

FOREIGN PATENT DOCUMENTS

| | | |
|---|---|---|
| WO | WO 98/25959 | 6/1998 |
| WO | WO 98/33913 | 8/1998 |

OTHER PUBLICATIONS

Martin BL et al., J. Biol Chem 1995, 270:26727–26730.
Solomon, B. et al., Proc. Natl. Acad. Sci., USA, vol. 93, 1996, pp. 452–455.
Solomon, B. et al., Proc. Natl. Acad. Sci, USA, vol. 94; 1997; pp. 4109–4112.
Frenkel D. et al., Journal of NeuroImmunology 106 (2000) 23–31.
Schenk D. et al., Nature, 400:173–177 (1999).
Kim S.H., et al. (1999) Nature Neurosc 2:984–988.
Duff K., TINS, Nov. 1999, Vol 22, (11):485–486.
Lansbury Jr., P., Current Opinion in Chemical Biology, 1997, 1:260–267.
Soto C., Molecular Medicine Today, 1999, 5:343–350.

*Primary Examiner*—Anne-Marie Falk
(74) *Attorney, Agent, or Firm*—Venable LLP; Shmuel Livnat

(57) ABSTRACT

Two novel mutant amyloid protein precursors (ABriPP and ADanPP) and their amyloid peptides (ABri and ADan) associated with Familial British Dementia and Familial Danish Dementia, respectively, are disclosed. Genetic constructs comprising DNA encoding these proteins is used to produced transgenic mammals that are useful models for neurological diseases associated with amyloid deposits, neurofibrillary tangles, non-neuritic plaques, neuronal degeneration and behavioral deficits characteristic of dementia and other symptoms of the human diseases. These models are used for testing potential therapeutic agents and methods. Also provided is a DNA-based test for detecting the mutations, the mutant proteins and peptides, antibodies specific for the proteins and peptides. Immunoassays permit detection of the mutant proteins, particularly in affected brain tissue, or detection of an antibody specific for a mutant peptide.

3 Claims, 5 Drawing Sheets

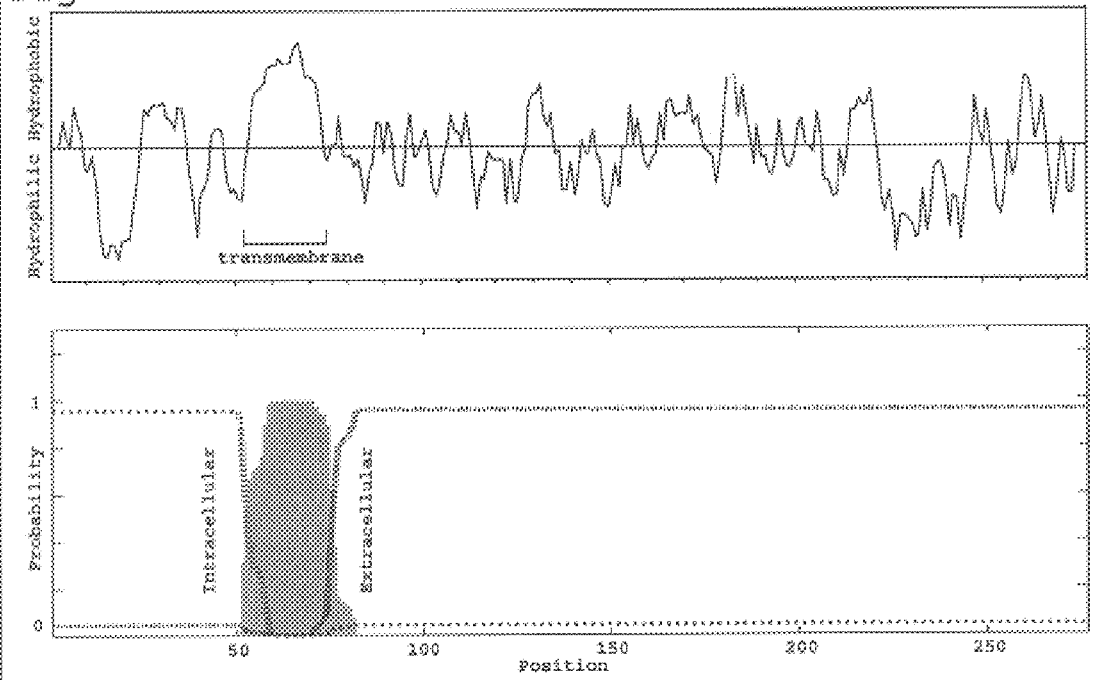
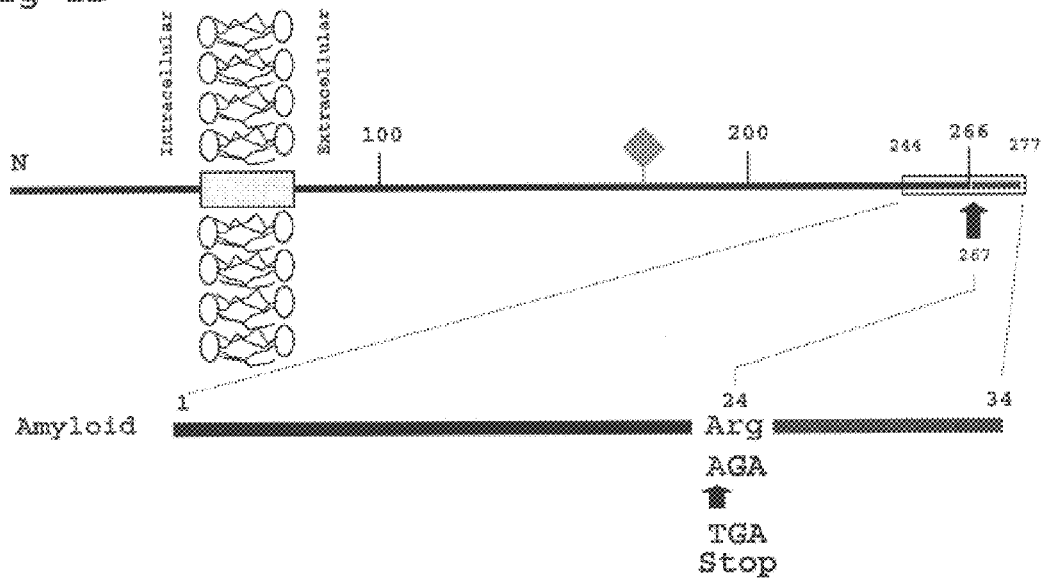

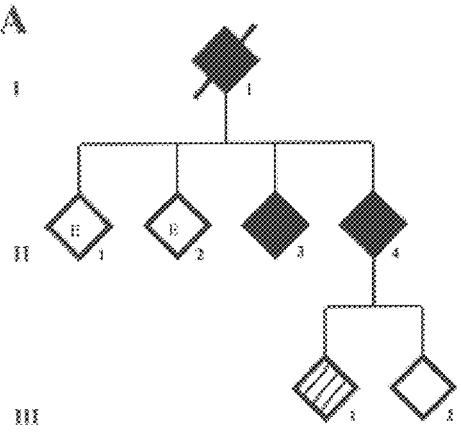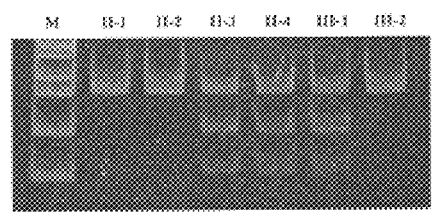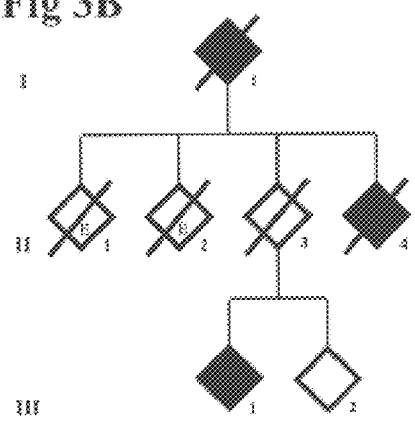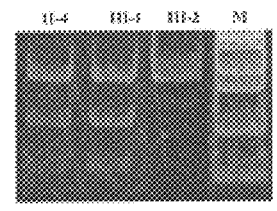

SEQUENCE LISTING

<160> NUMBER OF SEQ ID NOS: 28

<210> SEQ ID NO 1
<211> LENGTH: 1843
<212> TYPE: DNA
<213> ORGANISM: wild-type BriPP precursor protein
<221> NAME/KEY: CDS
<222> LOCATION: (171)..(968)

<400> SEQUENCE: 1

```
gcgagatccc taccgcagta gccgcctctg ccgccgcgga gcttcccgaa cctctcagcc      60
gcccggagcc gctcccggag cccggccgta gaggctgcaa tcgcagccgg gagcccgcag     120
cccgcgcccc gagcccgccg ccgcccttcg agggcgcccc aggccgcgcc atg gtg       176
                                                           Met Val
                                                             1 aag gtg acg ttc aac tcc gct ctg gcc cag aag gag gcc aag aag gac      224
Lys Val Thr Phe Asn Ser Ala Leu Ala Gln Lys Glu Ala Lys Lys Asp
          5                  10                  15 gag ccc aag agc ggc gag gag gcg ctc atc atc ccc ccc gac gcc gtc      272
Glu Pro Lys Ser Gly Glu Glu Ala Leu Ile Ile Pro Pro Asp Ala Val
     20                  25                  30 gcg gtg gac tgc aag gac cca gat gat gtg gta cca gtt ggc caa aga      320
Ala Val Asp Cys Lys Asp Pro Asp Asp Val Val Pro Val Gly Gln Arg
 35                  40                  45                  50 aga gcc tgg tgt tgg tgc atg tgc ttt gga cta gca ttt atg ctt gca      368
Arg Ala Trp Cys Trp Cys Met Cys Phe Gly Leu Ala Phe Met Leu Ala
                     55                  60                  65 ggt gtt att cta gga gga gca tac ttg tac aaa tat ttt gca ctt caa      416
Gly Val Ile Leu Gly Gly Ala Tyr Leu Tyr Lys Tyr Phe Ala Leu Gln
             70                  75                  80 cca gat gac gtg tac tac tgt gga ata aag tac atc aaa gat gat gtc      464
Pro Asp Asp Val Tyr Tyr Cys Gly Ile Lys Tyr Ile Lys Asp Asp Val
         85                  90                  95 atc tta aat gag ccc tct gca gat gcc cca gct gct ctc tac cag aca      512
Ile Leu Asn Glu Pro Ser Ala Asp Ala Pro Ala Ala Leu Tyr Gln Thr
    100                 105                 110 att gaa gaa aat att aaa atc ttt gaa gaa gaa gaa gtt gaa ttt atc      560
Ile Glu Glu Asn Ile Lys Ile Phe Glu Glu Glu Glu Val Glu Phe Ile
115                 120                 125                 130 agt gtg cct gtc cca gag ttt gca gat agt gat cct gcc aac att gtt      608
Ser Val Pro Val Pro Glu Phe Ala Asp Ser Asp Pro Ala Asn Ile Val
                135                 140                 145 cat gac ttt aac aag aaa ctt aca gcc tat tta gat ctt aac ctg gat      656
His Asp Phe Asn Lys Lys Leu Thr Ala Tyr Leu Asp Leu Asn Leu Asp
            150                 155                 160 aag tgc tat gtg atc cct ctg aac act tcc att gtt atg cca ccc aga      704
Lys Cys Tyr Val Ile Pro Leu Asn Thr Ser Ile Val Met Pro Pro Arg
        165                 170                 175 aac cta ctg gag tta ctt att aac atc aag gct gga acc tat ttg cct      752
Asn Leu Leu Glu Leu Leu Ile Asn Ile Lys Ala Gly Thr Tyr Leu Pro
    180                 185                 190
```

-continued

```
cag tcc tat ctg att cat gag cac atg gtt att act gat cgc att gaa    800
Gln Ser Tyr Leu Ile His Glu His Met Val Ile Thr Asp Arg Ile Glu
195                 200                 205                 210 aac att gat cac ctg ggt ttc ttt att tat cga ctg tgt cat gac aag    848
Asn Ile Asp His Leu Gly Phe Phe Ile Tyr Arg Leu Cys His Asp Lys
                215                 220                 225 gaa act tac aaa ctg caa cgc aga gaa act att aaa ggt att cag aaa    896
Glu Thr Tyr Lys Leu Gln Arg Arg Glu Thr Ile Lys Gly Ile Gln Lys
            230                 235                 240 cgt gaa gcc agc aat tgt ttc gca att cgg cat ttt gaa aac aaa ttt    944
Arg Glu Ala Ser Asn Cys Phe Ala Ile Arg His Phe Glu Asn Lys Phe
        245                 250                 255 gcc gtg gaa act tta att tgt tct tgaacagtca agaaaaacat tattgaggaa   998
Ala Val Glu Thr Leu Ile Cys Ser
    260                 265 aattaatatc acagcataac cccacccttt acattttgtg cagtgattat tttttaaagt  1058
cttctttcat gtaagtagca acagggctt  tactatcttt tcatctcatt aattcaatta  1118
aaaccattac cttaaaattt ttttctttcg aagtgtggtg tcttttatat ttgaattagt  1178
aactgtatga agtcatagat aatagtacat gtcaccttag gtagtaggaa gaattacaat  1238
ttctttaaat catttatctg gatttttatg ttttattagc attttcaaga agacggatta  1298
tctagagaat aatcatatat atgcatacgt aaaaatggac cacagtgact tatttgtagt  1358
tgttagttgc cctgctacct agtttgttag tgcatttgag cacacatttt aattttcctc  1418
taattaaaat gtgcagtatt ttcagtgtca aatatattta actatttaga gaatgatttc  1478
cacctttatg ttttaatatc ctaggcatct gctgtaataa tattttagaa atgtttggga  1538
atttaagaaa taacttgtgt tactaatttg tataacccat atctgtgcaa tggaatataa  1598
atatcacaaa gttgtttaac tagactgcgt gttgttttttc ccgtataata aaaccaaaga  1658
atagtttggt tcttcaaatc ttaagagaat ccacataaaa gaagaaacta tttttttaaaa 1718 attcacttct atatatacaa tgagtaaaat cacagatttt ttcttttaaat aaaaataagt 1778 cattttaata actaaaccag attctttgtg gatactatta aagtaacatt taagcctcaa  1838
ccttg                                                              1843
```

<210> SEQ ID NO 2
<211> LENGTH: 266
<212> TYPE: PRT
<213> ORGANISM: wild-type BriPP precursor protein

<400> SEQUENCE: 2

```
Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
            20                  25                  30

Ala Val Ala Val Asp Cys Lys Asp Pro Asp Val Val Pro Val Gly
        35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110
```

-continued

```
Gln Thr Ile Glu Glu Asn Ile Lys Ile Phe Glu Glu Val Glu
        115                 120                 125

Phe Ile Ser Val Pro Val Pro Glu Phe Ala Asp Ser Asp Pro Ala Asn
    130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
        195                 200                 205

Ile Glu Asn Ile Asp His Leu Gly Phe Phe Ile Tyr Arg Leu Cys His
    210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Ser
            260                 265
```

<210> SEQ ID NO 3
<211> LENGTH: 834
<212> TYPE: DNA
<213> ORGANISM: mutant ABri precursor protein
<221> NAME/KEY: CDS
<222> LOCATION: (1)..(831)

<400> SEQUENCE: 3

```
atg gtg aag gtg acg ttc aac tcc gct ctg gcc cag aag gag gcc aag    48
Met Val Lys Val Thr Phe Asn Ser Ala Leu Ala Gln Lys Glu Ala Lys
1               5                   10                  15 aag gac gag ccc aag agc ggc gag gag gcg ctc atc atc ccc ccc gac    96
Lys Asp Glu Pro Lys Ser Gly Glu Glu Ala Leu Ile Ile Pro Pro Asp
            20                  25                  30 gcc gtc gcg gtg gac tgc aag gac cca gat gat gtg gta cca gtt ggc   144
Ala Val Ala Val Asp Cys Lys Asp Pro Asp Asp Val Val Pro Val Gly
        35                  40                  45 caa aga aga gcc tgg tgt tgg tgc atg tgc ttt gga cta gca ttt atg   192
Gln Arg Arg Ala Trp Cys Trp Cys Met Cys Phe Gly Leu Ala Phe Met
    50                  55                  60 ctt gca ggt gtt att cta gga gga gca tac ttg tac aaa tat ttt gca   240
Leu Ala Gly Val Ile Leu Gly Gly Ala Tyr Leu Tyr Lys Tyr Phe Ala
65                  70                  75                  80 ctt caa cca gat gac gtg tac tac tgt gga ata aag tac atc aaa gat   288
Leu Gln Pro Asp Asp Val Tyr Tyr Cys Gly Ile Lys Tyr Ile Lys Asp
                85                  90                  95 gat gtc atc tta aat gag ccc tct gca gat gcc cca gct gct ctc tac   336
Asp Val Ile Leu Asn Glu Pro Ser Ala Asp Ala Pro Ala Ala Leu Tyr
            100                 105                 110 cag aca att gaa gaa aat att aaa atc ttg gaa gaa gaa gaa gtt gaa   384
Gln Thr Ile Glu Glu Asn Ile Lys Ile Leu Glu Glu Glu Glu Val Glu
        115                 120                 125 ttt atc agt gtg cct gtc cca gag ttt gca gat agt gat cct gcc aac   432
Phe Ile Ser Val Pro Val Pro Glu Phe Ala Asp Ser Asp Pro Ala Asn
    130                 135                 140 att gtt cat gac ttt aac aag aaa ctt aca gcc tat tta gat ctt aac   480
Ile Val His Asp Phe Asn Lys Lys Leu Thr Ala Tyr Leu Asp Leu Asn
```

```
ctg gat aag tgc tat gtg atc cct ctg aac act tcc att gtt atg cca    528
Leu Asp Lys Cys Tyr Val Ile Pro Leu Asn Thr Ser Ile Val Met Pro
            165                 170                 175 ccc aga aac cta ctg gag tta ctt att aac atc aag gct gga acc tat    576
Pro Arg Asn Leu Leu Glu Leu Leu Ile Asn Ile Lys Ala Gly Thr Tyr
            180                 185                 190 ttg cct cag tcc tat ctg att cat gag cac atg gtt att act gat cgc    624
Leu Pro Gln Ser Tyr Leu Ile His Glu His Met Val Ile Thr Asp Arg
            195                 200                 205 att gaa aac att gat cac ctg ggt ttc ttt att tat cga ctg tgt cat    672
Ile Glu Asn Ile Asp His Leu Gly Phe Phe Ile Tyr Arg Leu Cys His
210                 215                 220 gac aag gaa act tac aaa ctg caa cgc aga gaa act att aaa ggt att    720
Asp Lys Glu Thr Tyr Lys Leu Gln Arg Arg Glu Thr Ile Lys Gly Ile
225                 230                 235                 240 cag aaa cgt gaa gcc agc aat tgt ttc gca att cgg cat ttt gaa aac    768
Gln Lys Arg Glu Ala Ser Asn Cys Phe Ala Ile Arg His Phe Glu Asn
            245                 250                 255 aaa ttt gcc gtg gaa act tta att tgt tct aga aca gtc aag aaa aac    816
Lys Phe Ala Val Glu Thr Leu Ile Cys Ser Arg Thr Val Lys Lys Asn
            260                 265                 270 att att gag gaa aat taa                                            834
Ile Ile Glu Glu Asn
            275

<210> SEQ ID NO 4
<211> LENGTH: 277
<212> TYPE: PRT
<213> ORGANISM: mutant ABri precursor protein

<400> SEQUENCE: 4

Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
                20                  25                  30

Ala Val Ala Val Asp Cys Lys Asp Pro Asp Asp Val Val Pro Val Gly
            35                  40                  45

Gln Arg Arg Ala Trp Cys Trp Cys Met Cys Phe Gly Leu Ala Phe Met
    50                  55                  60

Leu Ala Gly Val Ile Leu Gly Gly Ala Tyr Leu Tyr Lys Tyr Phe Ala
65                  70                  75                  80

Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Leu Glu Glu Glu Val Glu
            115                 120                 125

Phe Ile Ser Val Pro Val Pro Glu Phe Ala Asp Ser Asp Pro Ala Asn
            130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
```

|  |  | 195 |  |  |  | 200 |  |  |  | 205 |  |
|---|---|---|---|---|---|---|---|---|---|---|---|

Ile Glu Asn Ile Asp His Leu Gly Phe Phe Ile Tyr Arg Leu Cys His
    210                    215                    220

Asp Lys Glu Thr Tyr Lys Leu Gln Arg Arg Thr Ile Lys Gly Ile
225                    230                    235                    240

Gln Lys Arg Glu Ala Ser Asn Cys Phe Ala Ile Arg His Phe Glu Asn
                245                    250                    255

Lys Phe Ala Val Glu Thr Leu Ile Cys Ser Arg Thr Val Lys Lys Asn
                260                    265                    270

Ile Ile Glu Glu Asn
        275

<210> SEQ ID NO 5
<211> LENGTH: 105
<212> TYPE: DNA
<213> ORGANISM: ABri protein
<221> NAME/KEY: CDS
<222> LOCATION: (1)..(102)

<400> SEQUENCE: 5

```
gaa gcc agc aat tgt ttc gca att cgg cat ttt gaa aac aaa ttt gcc      48
Glu Ala Ser Asn Cys Phe Ala Ile Arg His Phe Glu Asn Lys Phe Ala
1               5                   10                  15 gtg gaa act tta att tgt tct aga aca gtc aag aaa aac att att gag      96
Val Glu Thr Leu Ile Cys Ser Arg Thr Val Lys Lys Asn Ile Ile Glu
            20                  25                  30 gaa aat taa                                                          105
Glu Asn
```

<210> SEQ ID NO 6
<211> LENGTH: 34
<212> TYPE: PRT
<213> ORGANISM: ABri protein

<400> SEQUENCE: 6

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 7
<211> LENGTH: 834
<212> TYPE: DNA
<213> ORGANISM: mutant ADan precursor protein
<221> NAME/KEY: CDS
<222> LOCATION: (1)..(831)

<400> SEQUENCE: 7

```
atg gtg aag gtg acg ttc aac tcc gct ctg gcc cag aag gag gcc aag      48
Met Val Lys Val Thr Phe Asn Ser Ala Leu Ala Gln Lys Glu Ala Lys
1               5                   10                  15 aag gac gag ccc aag agc ggc gag gag gcg ctc atc atc ccc ccc gac      96
Lys Asp Glu Pro Lys Ser Gly Glu Glu Ala Leu Ile Ile Pro Pro Asp
            20                  25                  30 gcc gtc gcg gtg gac tgc aag gac cca gat gat gtg gta cca gtt ggc      144
Ala Val Ala Val Asp Cys Lys Asp Pro Asp Asp Val Val Pro Val Gly
        35                  40                  45 caa aga aga gcc tgg tgt tgg tgc atg tgc ttt gga cta gca ttt atg      192
Gln Arg Arg Ala Trp Cys Trp Cys Met Cys Phe Gly Leu Ala Phe Met
    50                  55                  60
```

|  |  |
|---|---:|
| ctt gca ggt gtt att cta gga gga gca tac ttg tac aaa tat ttt gca<br>Leu Ala Gly Val Ile Leu Gly Gly Ala Tyr Leu Tyr Lys Tyr Phe Ala<br>65                               70                     75                     80 | 240 |
| ctt caa cca gat gac gtg tac tac tgt gga ata aag tac atc aaa gat<br>Leu Gln Pro Asp Asp Val Tyr Tyr Cys Gly Ile Lys Tyr Ile Lys Asp<br>                       85                            90                           95 | 288 |
| gat gtc atc tta aat gag ccc tct gca gat gcc cca gct gct ctc tac<br>Asp Val Ile Leu Asn Glu Pro Ser Ala Asp Ala Pro Ala Ala Leu Tyr<br>                   100                          105                       110 | 336 |
| cag aca att gaa gaa aat att aaa atc ttg gaa gaa gaa gtt gaa<br>Gln Thr Ile Glu Glu Asn Ile Lys Ile Leu Glu Glu Glu Val Glu<br>              115                        120                       125 | 384 |
| ttt atc agt gtg cct gtc cca gag ttt gca gat agt gat cct gcc aac<br>Phe Ile Ser Val Pro Val Pro Glu Phe Ala Asp Ser Asp Pro Ala Asn<br>130                            135                    140 | 432 |
| att gtt cat gac ttt aac aag aaa ctt aca gcc tat tta gat ctt aac<br>Ile Val His Asp Phe Asn Lys Lys Leu Thr Ala Tyr Leu Asp Leu Asn<br>145                            150                      155                       160 | 480 |
| ctg gat aag tgc tat gtg atc cct ctg aac act tcc att gtt atg cca<br>Leu Asp Lys Cys Tyr Val Ile Pro Leu Asn Thr Ser Ile Val Met Pro<br>                    165                       170                       175 | 528 |
| ccc aga aac cta ctg gag tta ctt att aac atc aag gct gga acc tat<br>Pro Arg Asn Leu Leu Glu Leu Leu Ile Asn Ile Lys Ala Gly Thr Tyr<br>              180                      185                       190 | 576 |
| ttg cct cag tcc tat ctg att cat gag cac atg gtt att act gat cgc<br>Leu Pro Gln Ser Tyr Leu Ile His Glu His Met Val Ile Thr Asp Arg<br>                   195                       200 | 624 |
| att gaa aac att gat cac ctg ggt ttc ttt att tat cga ctg tgt cat<br>Ile Glu Asn Ile Asp His Leu Gly Phe Phe Ile Tyr Arg Leu Cys His<br>210                            215                       220 | 672 |
| gac aag gaa act tac aaa ctg caa cgc aga gaa act att aaa ggt att<br>Asp Lys Glu Thr Tyr Lys Leu Gln Arg Arg Glu Thr Ile Lys Gly Ile<br>225                            230                      235                       240 | 720 |
| cag aaa cgt gaa gcc agc aat tgt ttc gca att cgg cat ttt gaa aac<br>Gln Lys Arg Glu Ala Ser Asn Cys Phe Ala Ile Arg His Phe Glu Asn<br>                   245                       250                       255 | 768 |
| aaa ttt gcc gtg gaa act tta att tgt ttt aat ttg ttc ttg aac agt<br>Lys Phe Ala Val Glu Thr Leu Ile Cys Phe Asn Leu Phe Leu Asn Ser<br>260                            265                       270 | 816 |
| caa gaa aaa cat tat taa<br>Gln Glu Lys His Tyr<br>              275 | 834 |

<210> SEQ ID NO 8
<211> LENGTH: 277
<212> TYPE: PRT
<213> ORGANISM: mutant ADan precursor protein

<400> SEQUENCE: 8

Met Val Lys Val Thr Phe Asn Ser Ala Leu Ala Gln Lys Glu Ala Lys
1               5                   10                  15

Lys Asp Glu Pro Lys Ser Gly Glu Glu Ala Leu Ile Ile Pro Pro Asp
                20                  25                  30

Ala Val Ala Val Asp Cys Lys Asp Pro Asp Asp Val Val Pro Val Gly
            35                  40                  45

Gln Arg Arg Ala Trp Cys Trp Cys Met Cys Phe Gly Leu Ala Phe Met
        50                  55                  60

Leu Ala Gly Val Ile Leu Gly Gly Ala Tyr Leu Tyr Lys Tyr Phe Ala
65                  70                  75                  80

-continued

```
Leu Gln Pro Asp Asp Val Tyr Tyr Cys Gly Ile Lys Tyr Ile Lys Asp
                85                  90                  95

Asp Val Ile Leu Asn Glu Pro Ser Ala Asp Ala Pro Ala Ala Leu Tyr
            100                 105                 110

Gln Thr Ile Glu Glu Asn Ile Lys Ile Leu Glu Glu Glu Val Glu
            115                 120                 125

Phe Ile Ser Val Pro Val Pro Glu Phe Ala Asp Ser Asp Pro Ala Asn
        130                 135                 140

Ile Val His Asp Phe Asn Lys Lys Leu Thr Ala Tyr Leu Asp Leu Asn
145                 150                 155                 160

Leu Asp Lys Cys Tyr Val Ile Pro Leu Asn Thr Ser Ile Val Met Pro
                165                 170                 175

Pro Arg Asn Leu Leu Glu Leu Leu Ile Asn Ile Lys Ala Gly Thr Tyr
            180                 185                 190

Leu Pro Gln Ser Tyr Leu Ile His Glu His Met Val Ile Thr Asp Arg
            195                 200                 205

Ile Glu Asn Ile Asp His Leu Gly Phe Phe Ile Tyr Arg Leu Cys His
        210                 215                 220

Asp Lys Glu Thr Tyr Lys Leu Gln Arg Arg Glu Thr Ile Lys Gly Ile
225                 230                 235                 240

Gln Lys Arg Glu Ala Ser Asn Cys Phe Ala Ile Arg His Phe Glu Asn
                245                 250                 255

Lys Phe Ala Val Glu Thr Leu Ile Cys Phe Asn Leu Phe Leu Asn Ser
            260                 265                 270

Gln Glu Lys His Tyr
            275

<210> SEQ ID NO 9
<211> LENGTH: 105
<212> TYPE: DNA
<213> ORGANISM: ADan protein
<221> NAME/KEY: CDS
<222> LOCATION: (1)..(102)

<400> SEQUENCE: 9 gaa gcc agc aat tgt ttc gca att cgg cat ttt gaa aac aaa ttt gcc      48
Glu Ala Ser Asn Cys Phe Ala Ile Arg His Phe Glu Asn Lys Phe Ala
1               5                   10                  15 gtg gaa act tta att tgt ttt aat ttg ttc ttg aac agt caa gaa aaa      96
Val Glu Thr Leu Ile Cys Phe Asn Leu Phe Leu Asn Ser Gln Glu Lys
            20                  25                  30 cat tat tga                                                          105
His Tyr <210> SEQ ID NO 10
<211> LENGTH: 34
<212> TYPE: PRT
<213> ORGANISM: ADan protein

<400> SEQUENCE: 10

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
            20                  25                  30

His Tyr

<210> SEQ ID NO 11
```

```
<211> LENGTH: 11
<212> TYPE: PRT
<213> ORGANISM: ABri peptide

<400> SEQUENCE: 11

Cys Thr Val Lys Lys Asn Ile Ile Glu Glu Asn
1               5                   10

<210> SEQ ID NO 12
<211> LENGTH: 13
<212> TYPE: PRT
<213> ORGANISM: ADan peptide

<400> SEQUENCE: 12

Cys Phe Asn Leu Phe Leu Asn Ser Gln Glu Lys His Tyr
1               5                   10

<210> SEQ ID NO 13
<211> LENGTH: 34
<212> TYPE: PRT
<213> ORGANISM: ABri peptide

<400> SEQUENCE: 13

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
            20                  25                  30

Glu Asn

<210> SEQ ID NO 14
<211> LENGTH: 11
<212> TYPE: PRT
<213> ORGANISM: ABri peptide

<400> SEQUENCE: 14

Arg Thr Val Lys Lys Asn Ile Ile Glu Glu Asn
1               5                   10

<210> SEQ ID NO 15
<211> LENGTH: 12
<212> TYPE: PRT
<213> ORGANISM: ADan peptide

<400> SEQUENCE: 15

Phe Asn Leu Phe Leu Asn Ser Gln Glu Lys His Tyr
1               5                   10

<210> SEQ ID NO 16
<211> LENGTH: 18
<212> TYPE: PRT
<213> ORGANISM: FBD peptide
<221> NAME/KEY: UNSURE
<222> LOCATION: (3)..(3)
<223> OTHER INFORMATION: X represents an unknown residue
<221> NAME/KEY: UNSURE
<222> LOCATION: (7)..(8)
<223> OTHER INFORMATION: X represents an unknown residue
<221> NAME/KEY: UNSURE
<222> LOCATION: (12)..(12)
<223> OTHER INFORMATION: X represents an unknown residue
<221> NAME/KEY: UNSURE
<222> LOCATION: (17)..(17)
<223> OTHER INFORMATION: X represents an unknown residue

<400> SEQUENCE: 16

Ser Asn Xaa Phe Ala Ile Xaa Xaa Phe Glu Asn Xaa Phe Ala Val Glu
```

```
1               5              10              15
Xaa Leu

<210> SEQ ID NO 17
<211> LENGTH: 5
<212> TYPE: PRT
<213> ORGANISM: FBD peptide

<400> SEQUENCE: 17

His Phe Glu Asn Lys
1               5

<210> SEQ ID NO 18
<211> LENGTH: 10
<212> TYPE: PRT
<213> ORGANISM: FBD peptide

<400> SEQUENCE: 18

Phe Ala Val Glu Thr Leu Ile Cys Ser Arg
1               5              10

<210> SEQ ID NO 19
<211> LENGTH: 6
<212> TYPE: PRT
<213> ORGANISM: FBD peptide

<400> SEQUENCE: 19

Asn Ile Ile Glu Glu Asn
1               5

<210> SEQ ID NO 20
<211> LENGTH: 24
<212> TYPE: DNA
<213> ORGANISM: Primer

<400> SEQUENCE: 20
cgtgaagcca gcaattgttt cgca                                    24

<210> SEQ ID NO 21
<211> LENGTH: 22
<212> TYPE: DNA
<213> ORGANISM: Primer

<400> SEQUENCE: 21
agccctgttt gctacttaca tg                                      22

<210> SEQ ID NO 22
<211> LENGTH: 24
<212> TYPE: DNA
<213> ORGANISM: Primer

<400> SEQUENCE: 22
cgtgaagcca gcaattgttt cgca                                    24

<210> SEQ ID NO 23
<211> LENGTH: 19
<212> TYPE: DNA
<213> ORGANISM: Primer

<400> SEQUENCE: 23
acaaaatgta aagggtggg                                          19

<210> SEQ ID NO 24
```

```
<211> LENGTH: 4
<212> TYPE: PRT
<213> ORGANISM: consensus sequence

<400> SEQUENCE: 24

Glu Phe Arg His
1

<210> SEQ ID NO 25
<211> LENGTH: 7
<212> TYPE: PRT
<213> ORGANISM: epitope

<400> SEQUENCE: 25

Asp Ala Glu Phe Arg His Asp
1               5

<210> SEQ ID NO 26
<211> LENGTH: 6
<212> TYPE: PRT
<213> ORGANISM: consensus recognition sequence

<400> SEQUENCE: 26

Lys Gly Ile Gln Lys Arg
1               5

<210> SEQ ID NO 27
<211> LENGTH: 8
<212> TYPE: PRT
<213> ORGANISM: BriPP

<400> SEQUENCE: 27

Lys Gly Ile Gln Lys Arg Glu Ala
1               5

<210> SEQ ID NO 28
<211> LENGTH: 10
<212> TYPE: DNA
<213> ORGANISM: nucleotide insertion of ABri precursor gene

<400> SEQUENCE: 28
tttaatttgt                                                          10
```

MUTANT GENES IN FAMILIAL BRITISH DEMENTIA AND FAMILIAL DANISH DEMENTIA

This application claims benefit to U.S. Provisional Application No. 60/136,238, filed May 26, 1999.

STATEMENT OF RIGHTS TO INVENTIONS MADE UNDER FEDERALLY SPONSORED RESEARCH

This invention was funded in part by a grant from the National Institutes of Health (AG10953), which provides to the United States government certain rights in this invention.

BACKGROUND OF THE INVENTION

1. Field of the Invention

The present invention in the field of biochemistry, molecular genetics and medicine related to two newly discovered mutant amyloid precursor proteins (APP) and amyloid peptides that are associated, respectively, with Familial British Dementia and Familial Danish Dementia. Transgenic animals expressing these mutant proteins have progressive neurologic disease characterized by both behavioral and neuropathological changes as compared to non-transgenic age-matched controls. These animals are used to screen agents as potential therapeutics for any of a number of progressive degenerative neurologic syndromes characterized by neurofibrillary tangles and dementia. The invention is exemplified by transgenic mice which overexpress two types of mutant precursor protein (ABriPP and ADanPP) in brain tissue under control of tissue-specific gene regulatory sequences.

2. Description of the Background Art

Familial British Dementia (FBD)

FBD, previously designated familial cerebral amyloid angiopathy-British type (Plant, G T et al., *Brain* 113:721–747 (1990)), is an autosomal dominant condition characterized by dementia, progressive spastic tetraparesis and cerebellar ataxia with onset in the fifth decade of life (Altschul, S F et al., *Nucleic Acids Res.* 25:3389–3402 (1997); Worster-Drought, C et al., *J. Neurol. Psychopathol.* 14:27–34 (1933); Worster-Drought, C et al., *Brain* 63:237–254 (1940); Worster-Drought, C et al., *Brain* 67:38–43 (1944)). Pathological features include severe widespread cerebrovascular amyloidosis in the brain and spinal cord, nonneuritic amyloid plaques affecting cerebellum, hippocampus, amygdala and occasionally cerebral cortex, periventricular white matter changes, perivascular amyloid plaques and neurofibrillary degeneration in hippocampal neurons. The autosomal dominant mode of inheritance have been confirmed by the uninterrupted transmission from one generation to the next and by the segregation and sex ratios in a large family with more than 200 members encompassing seven generatons (Plant, G T et al., *Brain* 113:721–747 (1990)).

The biochemical basis of the disorder has remained elusive. It has been reported as an atypical form of familial Alzheimer's disease (Corsellis, J et al., *Brain* 77:571–587 (1954); Aikawa, H et al., *Ann. Neurol.* 17:297–300 (1985)), as an example of Gerstmann-Sträussler syndrome (Masters, C et al., *Brain* 104:535–558 (1981); Keohane, C et al., *J. Neurol. Neurosurg. Psych.* 48:1175–1178 (1985); Courten-Myers, G et al. *Neurology* 37:269–275 (1987); Pearlman, R L et al., *Neurology* 38:1249–1254 (1988)) and also regarded as a specific form of primary congophilic angiopathy (Vinters, H, *Stroke* 18:311–324 (1987)).

Classification attempts based on immunohistochemical analysis failed to demonstrate specific staining of the amyloid deposits with a large set of antibodies directed toward known amyloid molecules, although the lesions were immunoreactive for several amyloid associated proteins, i.e. apolipoproteins E and J and serum amyloid P-component (Ghiso, J et al., *J. Neurol. Sci.* 129:74–75 (1995)). Recently, C-terminal fragments of $\alpha$- and $\beta$-tubulin were reported to be associated with the amyloid lesions although the identification of the major component of the amyloid deposits remained unsettled (Baumann, M H et al., *Biochem. Biophys. Res. Commun.* 219:238–242 (1996)).

Familial Danish Dementia (FDD)

FDD is a familial condition characterized by progressive development of cataract and other ocular symptoms, hearing impairment, varying neurological symptoms, and dementia, usually complicated by paranoid reactions and occasional disturbances of consciousness.

The first family described with this disease originated from the Djursland peninsula northeast of the city of Aarhus, Denmark (Strömgrem E., "Heredopathia ophthalmo-oto-encephalica." In: Vinken P. J. et al., eds. *Handbook of Clinical Neurology*. Vol 42. Amsterdam: Elsevier 1981, pp 150–152). Cataract formation seems to be the first symptom, appearing before the age of 30. Impaired hearing tends to appear 10–20 years after the ocular symptoms. Ocular hemorrhages were also observed in some cases. Ataxia of a cerebellar type starts shortly after age of 40. These patients have intention tremor of the trunk and all four limbs as well as hypotonia with pendular reflexes. Paranoid psychosis usually develops after the age of 50, followed by dementia. Most affected individuals die in their 50's and 60's.

At autopsy, a uniform, diffuse atrophy of all parts of the brain is clearly observed in all patients. Histological examination shows a very severe chronic, diffuse encephalopathy, expressed most intensely in the cerebellum, the cerebral cortex and the white matter. Cranial nerves are extremely thin and nearly completely demyelinated. Widespread amyloid angiopathy is seen in blood vessels of the cerebrum, including the choroid plexus, cerebellum, retina and spinal cord. Neuritic plaques and sparse neurofibrillary tangles are present in the hippocampus which also shows some neuronal loss. The cerebral white matter also contains some ischemic lesions. As in FBD, described above, dementia is also attributed to both, vascular and parenchymal degenerative lesions. However, the nature of the amyloid deposits and the genetic defect remains unknown.

A number of investigators have produced transgenic mice that are intended to serve as model for Alzheimer's disease (AD), for example U.S. Pat. No. 5,387,742, U.S. Pat. No. 5,612,486, U.S. Pat. No. 5,811,633, U.S. Pat. No. 5,849,999 and U.S. Pat. No. 5,877,399. Even as AD models, each of these has shortcomings. None of these transgenic mice models express the gene associated with FBD or FDD. Moreover, none of them provide the combination of neuropathological changes desired in a robust model of human degenerative dementias, namely amyloid deposition and neurofibrillary tangles and neuronal degeneration.

Key embodiments of the present invention are designed to overcome this deficiency, provide a useful animal model not only of the two specific familial dementias described, but more importantly, to serve as general model for a group of human degenerative neurological diseases that include dementia.

Citation of the above documents is not intended as an admission that any of the foregoing is pertinent prior art. All statements as to the date or representation as to the contents

SUMMARY OF THE INVENTION

The present invention is directed to an isolated wild-type amyloid precursor protein, BriPP, or a mutant ABriPP or ADanPP, the sequences and structures of which are described herein. Also included is a peptide that is a fragment of the protein, more preferably the mutant fragment that is the amyloid peptide, a 34 mer from the C-terminus of the mutant protein. In addition to the proteins and peptides, the invention includes functional derivatives such as amino acid sequence variants or chemical derivatives of the wild-type or mutant protein or peptide.

The present invention is directed to an antibody, polyclonal or monoclonal (mAb), specific for the mutant peptide described above, and to immunoassays to detect the mutant protein or peptide, or to detect the presence of the antibody in a sample.

In another embodiment, the invention provides DNA molecules encoding the wild-type or mutant protein or peptide. Preferably, the DNA is an expression vector wherein the coding sequence is operatively linked to a promoter and control sequences that result in selective expression of the DNA in the brain when the DNA is provided as a transgene to a mammal, preferably a mouse.

Also provided is a DNA-based assay to detect the presence of the ABri or ADan mutation in a subject suspected of harboring the mutation. The assay detects either a XbaI restriction site added as a result of the mutation, or the presence of additional DNA fragments compared to wild-type in a PCR amplified preparation of DNA.

Among the most preferred embodiments is a transgenic mammal, preferably a rodent, more preferably a mouse, having a diploid genome comprising a transgene encoding a heterologous amyloid precursor polypeptide having the British (ABriPP) or Danish (ADanPP) mutation, wherein the transgene is expressed to produce a human precursor polypeptide having the indicated mutation, and wherein the polypeptide is processed to the 34 amino acid amyloid peptide ABri or ADan, respectively in a sufficient amount to be detectable in the brain of the transgenic rodent.

Expression of the DNA constructs of the invention as a transgene in the mammal, preferably mouse, results in brain amyloid deposits, neurofibrillary tangles, non-neuritic plaque formation degeneration of neurons in the hippocampus and/or cerebellum; the mice exhibit cognitive impairment. The transgene is integrated in somatic and germ cells. The above transgene may be nonhomologously integrated.

The above construct is transcribed in brain cells of the mouse to form mRNA which is translated into detectable levels of ABriPP or ADanPP protein.

Also included are progeny of the above transgenic mice, wherein the genome of the progeny animal comprises the ABriPP or ADanPP transgene comprising operatively linked regulatory sequences as described below, wherein neural expression of the transgene produces impaired performance of the progeny mice in memory and learning tests and induces abnormal neuropathology as described below, in the progeny's brain, wherein the impaired performance and the abnormal neuropathology are in comparison with control mice. The transgenic mouse may be one wherein its non-transgenic ancestor is from a strain having greater longevity as compared with other strains of mice.

As a result of the expression of the transgene, the transgenic mouse preferably suffers from progressive neurological disease characterized as an age-dependent decline in performance in memory and learning tests, non-neuritic amyloid plaques that are detectable by Congo red staining in the mouse's brain, wherein the decline in performance and amyloid plaques are in comparison with control mice.

The transgenic animals produced in accordance with the present invention are intended to provide an experimental medium for elucidating aspects of the molecular pathogenesis of FBD, FDD or other neurodegenerative diseases that include dementia, and to serve as tools for screening drugs that may have potential application as therapeutic agents to prevent or limit amyloid accumulation, development of neurofibrillary tangles, neuronal degeneration, and therefore reduce or prevent the behavioral and physical symptoms consequent to such pathophysiology.

The invention includes cells from the above transgenic mouse or progeny, which cells comprise the mutant transgene DNA and in which expression of the DNA construct results in the production of detectable levels of the precursor proteins or amyloid peptides thereof.

This invention includes a method for enhancing neurodegeneration in the brain of a transgenic mouse, the method comprising:

(a) introducing the above DNA expression construct into a mouse embryo thereby producing a transgenic mouse embryo whose genome comprises the DNA sequence;

(b) developing the transgenic mouse embryo into a mouse, wherein expression of the DNA sequence results in an earlier onset of neurodegeneration in the brain of the transgenic mouse as compared to a control transgenic mouse that expresses (i) the wild-type human BriPP or (ii) endogenously expresses the murine homologue of BriPP.

The present invention is further directed to a method for identifying an agent that inhibits neurodegeneration in FBD, FDD or in a neurodegenerative disease having the symptoms of amyloid deposition, non-neuritic plaque formation, neurofibrillary tangles, the method comprising;

(a) providing a transgenic mouse as described above, (b) administering to the mouse a candidate agent; and (c) assaying or observing a decrease in neurodegeneration, or any of the indicated neuropathological signs, in the brain of this mouse as compared to neurodegeneration or neuropathological signs in the brain of a mouse of step (a) that is not administered the compound.

The decreased neuropathologic findings as a result of administering an agent that is positive in the transgenic model includes one or more of: reduction in number of ABri or ADan amyloid deposits; a reduction of hypertrophic gliosis in cortico-limbic structures; a reduction of diminished 2-deoxyglucose uptake or utilization in cortico-limbic structures of the brain.

BRIEF DESCRIPTION OF THE DRAWINGS

FIGS. 1A and 1B present information and a model of the ABri precursor molecule as a cell surface glycoprotein. The top panel of FIG. 1 *2A shows a hydropathy plot of the putative ABri precursor protein (BriPP) using the hydrophobicity indices of Kyte and Doolittle with a calculation window of 7 residues. The bottom panel of FIG. 1A provides a transmembrane prediction analysis according to Sonnhammer et al. (ISMB98: 175–182 (1998)), performed at the web site of the Prediction Servers, Center for Biological Sequence Analysis (http://www.cbs.dtu.dk).

FIG. 1B presents a model for the structural organization of the putative ABri precursor molecule (BriPP). Analysis predicted the presence of a putative single transmembrane spanning domain between amino acid residues 52 and 74, with the long C-terminal part being extracellular (type II integral transmembrane protein). The diamond ♦ indicates a single potential N-glycosylation site at position 170. The box enclosing positions 244 to 277 indicates the location of the 34-residue ABri amyloid peptide of the mutated precursor protein ABriPP. The up-arrow indicates the mutated codon (position 267) resulting in the change of a stop codon TGA into an arginine residue (AGA). The next in-frame stop codon is at a position that would correspond to residue 278.

FIGS. 3A and 3B provide an analysis of nucleotide substitutions in the ABriPP gene. Members of the British family pedigree are shown. Roman numerals indicate different generations. Individual IA(1) is a descendent of affected case III(1), and individual IB(1) is a descendent of affected case III(3) as described by Plant et al. (supra). M indicates φX174 RF DNA Hae III fragments marker. Affected members (filled symbols) and at-risk members (hatched symbols) carried one allele with the XbaI site. The XbaI site was not present in all obligate escapees (open symbol with E) and all normal controls (not shown).

DESCRIPTION OF THE PREFERRED EMBODIMENTS

Figure 2:
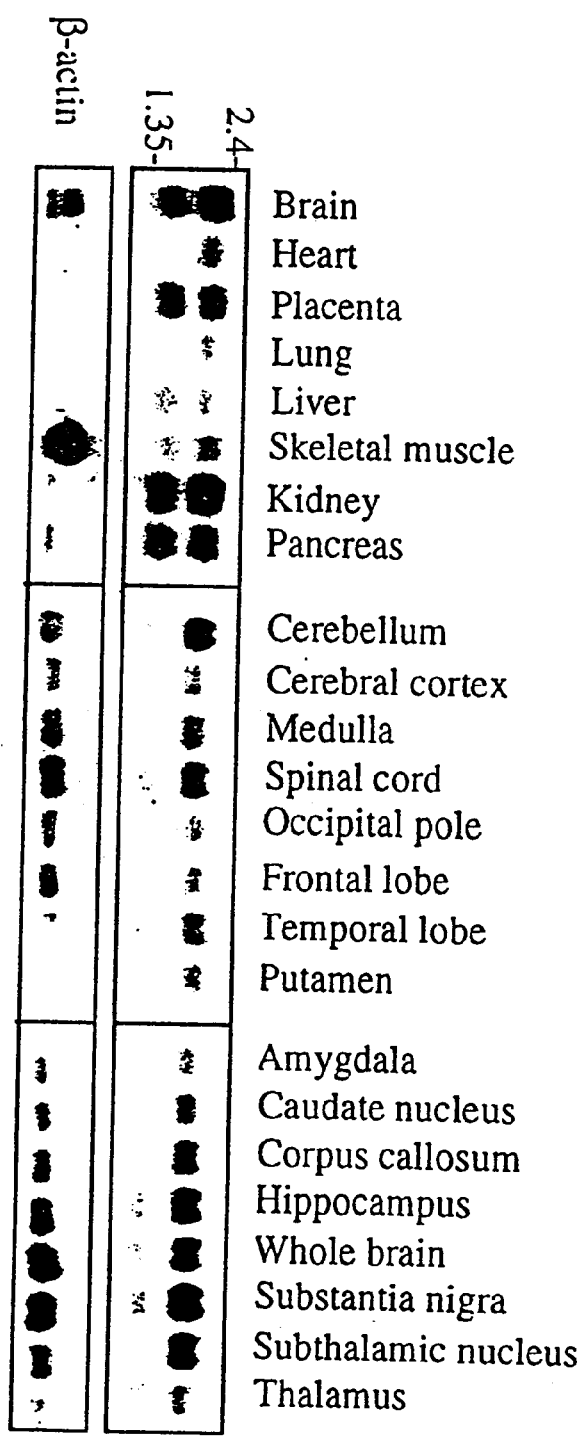
FIG. 2 is a series of Northern blots showing the expression of the ABriPP transcript. The DNA probe was hybridized to northern blots (Clontech, CA) containing 2 μg per lane of human poly-A+mRNA isolated from different tissues and various regions of the human brain. Filters were prehybridized at 42° C. for 3 h in 5×SSC, 5×Denhart's, 20 mM NaH$_2$PO$_4$, 0.2% SDS, 20% formamide and 250 μg/ml salmon sperm DNA. Hybridization was performed for 16 h at 42° C. in the same solution containing the $^{32}$P-labeled probe at 1×10$^6$ cpm/ml. Membranes were washed at 42° C. in 2×SSPE containing 0.1% SDS. Blots were rehybridized in ExpressHyb solution (Clontech) at 68° C. for 1 h using the $^{32}$P-labeled β-actin probe.

The present inventors have discovered two separate mutations of independent origin in a protein they have discovered and named BriPP (as it is the precursor protein of amyloid peptide found deposited in patients with Familial British Dementia (FBD). The nucleotide [SEQ ID NO:1] and deduced amino acid [SEQ ID NO:2] sequence of the wild-type BriPP precursor protein are shown in Table 1. The coding sequence runs from nucleotide 0–798 (if including the ATG start codon) Or from 4–798 (if excluding this codon).

One mutation results in ABriPP, a 277 amino acid mutant precursor protein of the mutant amyloid peptide termed ABri.

The nucleotide [SEQ ID NO:3] and amino acid [SEQ ID NO:4] sequences of the full length mutant ABri precursor proteins is shown in Table 2. The nucleotide sequence includes an additional seven non-coding nucleotides 5' from the initiation codon. This nucleotide sequence comprises a preferred insert for expression vectors that are used to produce transgenic animals expressing this mutant precursor protein. The nucleotide [SEQ ID NO:5] and amino acid [SEQ ID NO:6] sequences of the ABri peptide, which has 34 residues, appear in Table 3.

TABLE 1

Nucleotide sequence [SEQ ID NO: 1] and predicted amino acid sequence [SEQ ID NO:2] of a cDNA clone encoding the normal precursor (BriPP), of the ABri amyloid protein

| SEQUENCE (nucleotide and aa) | aa# | Nuc#C |
|---|---|---|
| gcgagatccctaccgcagtagccgcctctgccgcc | | −136 |
| gcggagcttcccgaacctctcagccgcccggagccgctcccggag | | −91 |
| cccggccgtagaggctgcaatcgcagccggyagcccgcagcccgc | | 46 |
| gccccgagcccgccgccgcccttcgagggcgcccaggccgcgcc | | −1 |
| atggtgaaggtgacgttcaactccgctctggcccagaaggaggcc | | 45 |
|  M  V  K  V  T  F  N  S  A  L  A  Q  K  E  A | 15 | |
| aagaaggacgagcccaagagcggcgaggaggcgctcatcatcccc | | 90 |
|  K  K  D  E  P  K  S  G  E  E  A  L  T  I  P | 30 | |
| cccgacgccgtcgcggtggactgcaaggacccagatgatgtggta | | 135 |
|  P  D  A  V  A  V  D  C  K  D  P  D  D  V  V | 45 | |
| ccagttggccaaagaagagcctggtgttggtgcatgtgctttgga | | 180 |
|  P  V  G  O  R  R  |A  W  C  A  C  M  C  F  G| | 60 | |
| kctagcatttatgcttgcaggtgttattctaggaggagcatacttg | | 225 |
| |L  A  F  M  L  A  G  V  I  L  G  G  A  Y  L| | 75 | |
| tacaaatattttgcacttcaaccagatgacgtgtactactgtgga | | 270 |
|  Y  K  Y  F  A  L  Q  P  D  D  V  Y  Y  C  G | 90 | |
| ataaagtacatcaaagatgatgtcatcttaaatgagccctctgca | | 315 |

TABLE 1-continued

Nucleotide sequence [SEQ ID NO: 1] and predicted amino acid sequence [SEQ ID NO:2] of a cDNA clone encoding the normal precursor (BriPP), of the ABri amyloid protein

| SEQUENCE (nucleotide and aa) | aa# | Nuc#C |
|---|---|---|
| I K Y I K D D V I L N E P S A | 105 | |
| gatgccccagctgctctctaccagacaattgaagaaaatattaaa | | 360 |
| D A P A A L Y Q T I E E N I K | 120 | |
| atctttgaagaagaagaagttgaatttatcagtgtgcctgtccca | | 405 |
| I F E E E V E F I S V P V P | 135 | |
| gagtttgcagatagtgatcctgccaacattgttcatgactttaac | | 450 |
| E F A D S D P A N I V H D F N | 150 | |
| aagaaacttacagcctatttagatcttaacctggataagtgctat | | 495 |
| K K L T A Y L D L N L D K O Y | 165 | |
| gtgatccctctgaacacttccattgttatgccacccagaaaccta | | 540 |
| V I P L <u>N</u> T S I V M P P R N L | 180 | |
| ctggagttacttattaacatcaaggctggaacctatttgcctcag | | 585 |
| L E L L I N I K A G T Y L P Q | 195 | |
| tcctatctgattcatgagcacatggttattactgatcgcattgaa | | 630 |
| S Y L I H E H M V I T D R I E | 210 | |
| Aacattgatcacctgggtttctttatttatcgactgtgtcatgac | | 675 |
| N I D H L G F F I Y R L C H D | 225 | |
| Aaggaaacttacaaactgcaacgcagagaaactattaaaggtatt | | 720 |
| K E T Y K L Q R R E T I K G I | 240 | |
| cagaaacgtgaagccagcaattgtttcgcaattcggcattttgaa | | 765 |
| Q K R E A S N C F A I R H F E | 255 | |
| aacaaatttgccgtggaaactttaatttgttcttgaacagtcaag | | 810 |
| N K F A V E T L I C S — | 266 | |
| aaaaacattattgaggaaaattaatatcacagcataaccccaccc | | 855 |
| tttacattttgtgcagtgattatttttaaagtcttctttcatgt | | 900 |
| aagtagcaaacagggctttactatctttttcatctcattaattcaa | | 945 |
| <u>ttaaa</u>accattaccttaaaatttttttctttcgaagtgtggtgtc | | 990 |
| ttttatatttgaattagtaactgtatgaagtcatagataatagta | | 1035 |
| catgtcaccttaggtagtaggaagaattacaatttctttaaatca | | 1080 |
| tttatctggattttatgttttattagcattttcaagaagacgga | | 1125 |
| ttatctagagaataatcatatatatgcatacgtaaaaatgcaca | | 1170 |
| cagtgacttattgtagttgttagttgccctgctacctagtttgt | | 1215 |
| tagtgcatttgagcacaaattttaattttcctctaattaaaatgt | | 1260 |
| gcagtattttcagtgtcaaatatatttaactatttagagaatgat | | 1305 |
| ttccacctttatgttttaatatcctaggcatctgctgtaataata | | 1350 |
| ttttagaaaatgtttggaatttaagaaataacttgtgttactaat | | 1395 |
| ttgtataacccatatctgtgcaatggaa<u>tataaa</u>atcacaaagt | | 1440 |
| tgtttaactagactgcgtgttgttttccccgtat<u>aataaa</u>accaa | | 1485 |
| agaatagtttggttcttcaaatcttaagagaatccacataaaaga | | 1530 |
| agaaactatttttaaaaattcacttctatatatacaatgagtaa | | 1575 |
| aatcaccagatttttctttt<u>aataaa</u>aataagtcatttaataac | | 1620 |
| taaaccagattctttgtggatact<u>attaaa</u>gtaacatttaagcct | | 1665 |
| caaccttg | | 1673 |

TABLE 2

ABri Precursor Protein (ABriPP)

| SEQUENCE (nucleotide and aa) | aa # | Nuc # |
|---|---|---|
| ccgcgcc | | −1 |
| atg gtg aag gtg acg ttc aac tcc gct ctg gcc cag aag gag gcc | | 45 |
| M V K V T F N S A L A Q K E A | 15 | |
| aag aag gac gagccc aag agc ggc gag gag gcg ctc atc atc ccc | | 90 |
| K K D E P K S G E E A L I I P | 30 | |
| ccc gac gcc gtc gcg gtg gac tgc aaq gac cca gat gat gtg gta | | 135 |

TABLE 2-continued

ABri Precursor Protein (ABriPP)

| SEQUENCE (nucleotide and aa) | | | | | | | | | | | | aa # | Nuc # |
|---|---|---|---|---|---|---|---|---|---|---|---|---|---|
| P | D | A | V | A | V | D | C | K | D | P | D | D | V | V | 45 | |

| | | | | | | | | | | | | | |
|---|---|---|---|---|---|---|---|---|---|---|---|---|---|
| cca | gtt | ggc | caa | aga | aga | gcc | tgg | tgt | tgg | tgc | atg | tgc | ttt | gga | | 180 |
| P | V | G | Q | R | R | A | W | C | W | C | M | C | F | G | 60 | |

| cta | gca | ttt | atg | ctt | gca | ggt | gtt | att | cta | gga | gga | gca | tac | ttg | | 225 |
| L | A | F | M | L | A | G | V | I | L | G | G | A | Y | L | 75 | |

| tac | aaa | tat | ttt | gca | ctt | caa | cca | gat | gac | gtg | tac | tac | tgt | gga | | 270 |
| Y | K | Y | F | A | L | Q | P | D | D | V | Y | Y | C | G | 90 | |

| ata | aag | tac | atc | aaa | gat | gat | gtc | atc | tta | aat | gag | ccc | tct | gca | | 315 |
| I | K | Y | I | K | D | D | V | I | L | N | E | P | S | A | 105 | |

| gat | gcc | cca | gct | gct | ctc | tac | cag | aca | att | gaa | gaa | aat | att | aaa | | 360 |
| D | A | P | A | A | L | Y | Q | T | I | E | E | N | I | K | 120 | |

| atc | ttg | gaa | gaa | gaa | gaa | gtt | gaa | ttt | atc | agt | gtg | cct | gtc | cca | | 405 |
| I | F | E | E | E | E | V | E | F | I | S | V | P | V | P | 135 | |

| gag | ttt | gca | gat | agt | gat | cct | gcc | aac | att | gtt | cat | gac | ttt | aac | | 450 |
| E | F | A | D | S | D | P | A | N | I | V | H | D | F | N | 150 | |

| aag | aaa | ctt | aca | gcc | tat | tta | gat | ctt | aac | ctg | gat | aag | tgc | tat | | 495 |
| K | K | L | T | A | Y | L | D | L | N | L | D | K | C | Y | 165 | |

| gtg | atc | cct | ctg | aac | act | tcc | att | gtt | atg | cca | ccc | aga | aac | cta | | 540 |
| v | i | P | L | N | T | S | I | V | M | P | P | R | N | L | 180 | |

| ctg | gag | tta | ctt | att | aac | atc | aag | gct | gga | acc | tat | ttg | cct | cag | | 585 |
| L | E | L | L | I | N | I | K | A | G | T | Y | L | P | Q | 195 | |

| tcc | tat | ctg | att | cat | gag | cac | atg | gtt | att | act | gat | cgc | att | gaa | | 630 |
| S | Y | L | I | H | E | H | M | V | I | T | D | R | I | E | 210 | |

| aac | att | gat | cac | ctg | ggt | ttc | ttt | att | tat | cga | ctg | tgt | cat | gac | | 675 |
| N | I | D | H | L | G | F | F | I | Y | R | L | C | H | D | 225 | |

| aag | gaa | act | tac | aaa | ctg | caa | cgc | aga | gaa | act | att | aaa | ggt | att | | 720 |
| K | E | T | Y | K | L | Q | R | R | E | T | I | K | G | I | 240 | |

| cag | aaa | cgt | gaa | gcc | agc | aat | tgt | ttc | gca | att | cgg | cat | ttt | gaa | | 765 |
| Q | K | R | E | A | S | N | C | F | A | I | R | H | F | E | 255 | |

| aac | aaa | ttt | gcc | gtg | gaa | act | tta | att | tgt | tct | aga | aca | gtc | aag | | 810 |
| N | K | F | A | V | E | T | L | I | C | S | R | T | V | K | 270 | |

| aaa | aac | att | att | gag | gaa | aat | [taa] | | | | | | | | | 821 |
| K | N | I | I | E | E | N | — | | | | | | | | 277 | |

TABLE 3

Nucleotide (SEQ ID NO:3) and amino acid (SEQ ID NO:4) sequences of the 34-residue mutant ABri mutant amyloid peptide

```
gaagccagcaattgtttcgcaattcggcattttgaaaacaaattt
 E   A   S   N   C   F   A   I   R   H   F   E   N   K   F
 1                                                      15 gccgtggaaactttaatttgttctagaacagtcaagaaaaacatt
 A   V   E   T   L   I   C   S   R   T   V   K   K   N   I
 16                          24                          30
                            (267)

attgaggaaaattaa
 I   E   E   N   —
 31        34
```

Amyloid was isolated from leptomeningeal and parenchymal deposits of case V41 (Plant et al., supra) using a combination of formic acid/DS solubilization and gel filtration chromatography. The order of the peptides was assessed by the homology searches of EST-DNA databank using the BLAST algorithm. A point mutation at stop codon 267, indicated in bold, results in the presence of arginine (R) at this position and an open reading frame of 277 amino acids.
The C-teminal peptide NIIEEN exhibited perfect homology with a 3'-untranslated segment located after the stop codon 267 and immiediately before the next in-frame stop codon at position 278 (indicated in bold, italic).

TABLE 3-continued

Nucleotide (SEQ ID NO:3) and amino acid (SEQ ID NO:4) sequences of the 34-residue mutant ABri mutant amyloid peptide According to mass spectrometric analysis and the sequence data, the ABri amyloid peptide is encoded by the last 102 nucleotides of the mutated precursor. The XbaI restriction site introduced by the mutation at nucleotide 799 (codon 267) is underlined.

The second mutation, responsible for Familial Danish Dementia (FDD), results in a mutant BriPP that the inventors have named ADanPP, also having 277 amino acids. The nucleotide [SEQ ID NO:7] and amino acid [SEQ ID NO:8] sequences of the full length mutant ADan precursor protein ("ADanPP") are shown in Table 4. The nucleotide sequence includes an additional seven non-coding nucleotides 5' from the initiation codon. This nucleotide sequence comprises a preferred insert for expression vectors that are used to produce transgenic animals expressing this mutant precursor protein.

This precursor generates a mutant amyloid peptide of 34 amino acids termed ADan. The nucleotide [SEQ ID NO:9] and amino acid [SEQ ID NO:10] sequences of the ADan peptide appear in Table 5.

TABLE 5

Nucleotide (SEQ ID NO:9) and amino acid sequence (SEQ ID NO:10) of the 34-residue ADan mutant amyloid peptide

```
gaagccagcaattgtttcgcaattcggcattttgaaaacaaattt
 E  A  S  N  C  F  A  I  R  H  F  E  N  K  F
 1                                           15 gccgtggaaactttaatttgttttaatttgttcttgaacagtcaa
 A  V  E  T  L  I  C  F  N  L  F  L  N  S  Q
16                                           30 gaaaaacattattga
 E  K  H  Y  —
31         34
```

The nucleotide insertion after codon 265 is underlined. The insertion results in an open reading frame of 277 amino acids which constitute the mutated precursor protein termed ADanPP.

Aspects of the present invention are disclosed in a paper entitled "A decamer duplication in the 3' region of the BRI gene originates a new amyloid peptide that is associated with dementia in a Danish kindred," co-authored by co-inventors Jorge Ghiso, Ruben Vidal and Blas Frangione (along with others) that appeared in *Proc. Natl. Acad. Sci. USA*. 97:4920–4925 (Apr. 25, 2000). That publication is hereby incorporated by reference in its entirety.

TABLE 4

ADan Precursor Protein (ADanPP)

SEQUENCE (nucleotide and aa)                                    aa #   Nuc #

```
                                           ccgcgcc              -1
atg gtg aag gtg acg ttc aac tcc gct ctg gcc cag aag gag gcc      45
 M   V   K   V   T   F   N   S   A   L   A   Q   K   E   A   15
aag aag gac gag ccc aag agc ggc gag gag gcg ctc atc atc ccc      90
 K   K   D   E   P   K   S   G   E   E   A   L   I   I   P   30
ccc gac gcc gtc gcg gtg gac tgc aag gac cca gat gat gtg gta     135
 P   D   A   V   A   V   D   C   K   D   P   D   D   V   V   45
cca gtt ggc caa aga aga gcc tgg tgt tgg tgc atg tgc ttt gga     180
 P   V   G   Q   R   R   A   W   C   W   C   M   C   F   G   60
cta gca ttt atg ctt gca ggt gtt att cta gga gga gca tac ttg     225
 L   A   F   M   L   A   G   V   I   L   G   G   A   Y   L   75
tac aaa tat ttt gca ctt caa cca gat gac gtg tac tac tgt gga     270
 Y   K   Y   F   A   L   Q   P   D   D   V   Y   Y   C   G   90
ata aag tac atc aaa gat gat gtc atc tta aat gag ccc tct gca     315
 I   K   Y   I   K   D   D   V   I   L   N   E   P   S   A  105
gat gcc cca gct gct ctc tac cag aca att gaa gaa aat att aaa     360
 D   A   P   A   A   L   Y   Q   T   I   E   E   N   I   K  120
atc ttg gaa gaa gaa gaa gtt gaa ttt atc agt gtg cct gtc cca     405
 I   L   E   E   E   E   V   E   F   I   S   V   P   V   P  135
gag ttt gca gat agt gat cct gcc aac att gtt cat gac ttt aac     450
 E   F   A   D   S   D   P   A   N   I   V   H   D   F   N  150
aag aaa ctt aca gcc tat tta gat ctt aac ctg gat aag tgc tat     495
 K   K   L   T   A   Y   L   D   L   N   L   D   K   C   Y  165
gtg atc cct ctg aac act tcc att gtt atg cca ccc aga aac cta     540
 V   I   P   L   N   T   S   I   V   M   P   P   R   N   L  180
ctg gag tta ctt att aac atc aag gct gga acc tat ttg cct cag     585
 L   E   L   L   I   N   I   K   A   G   T   Y   L   P   Q  195
tcc tat ctg att cat gag cac atg gtt att act gat cgc att gaa     630
 S   Y   L   I   H   E   H   M   V   I   T   D   R   I   E  210
aac att gat cac ctg ggt ttc ttt att tat cga ctg tgt cat gac     675
 N   I   D   H   L   G   F   F   I   Y   R   L   C   H   D  225
aag gaa act tac aaa ctg caa cgc aga gaa act att aaa ggt att     720
 K   E   T   Y   K   L   Q   R   R   E   T   I   K   G   I  240
cag aaa cgt gaa gcc agc aat tgt ttc gca att cgg cat ttt gaa     765
 Q   K   R   E   A   S   N   C   F   A   I   R   H   F   E  255
aac aaa ttt gcc gtg gaa act tta att tgtk ttt aat ttg ttc ttg    810
 N   K   F   A   V   E   T   L   I   C   F   N   L   F   L  270
aac agt caa gaa aaa cat tat [taa]                               831
 N   S   Q   E   K   H   Y                                   277
```

The present invention provides a transgenic non-human eukaryotic animal, described in greater detail below, whose germ cells and somatic cells contain DNA encoding either ABriPP or ADanPP mutant amyloid precursor protein. These mutant DNA sequences have been introduced into the animal, or an ancestor of the animal, at an embryonic stage.

Transgenic mice manifest an age-related neurological disorder characterized by amyloid deposition, neurofibrillary tangles, neuronal degeneration, behavioral deficits and early death. An acceleration of this disorder occurs in mice expressing ABriPP (or ADanPP) under the control of expression control sequences, especially promoters, that result in significant overproduction, or in mice that have integrated high copy numbers of the transgene or in which the transgene has integrated in particular positions in the genome.

Pathological changes of particular interest in the brains of these animals occur in cortico-limbic areas, the cerebellum and the vasculature. Also of interest in ADanPP transgenic animals is the retina and brain and ear structures associated with the hearing loss observed in the human disease.

Recombinant Expression of ABriPP and ADanPP Proteins

Most of the techniques which are used to transform cells, construct vectors, extract messenger RNA, prepare cDNA, and the like are widely practiced in the art, and practitioners are familiar with the standard resource materials as well as specific conditions and procedures. However, for convenience, some of the information provided below may serve as an additional guideline.

Transgenic animals of the invention are constructed using an expression cassette which includes in the 5'-3' direction of transcription, a transcriptional and translational initiation region associated with gene expression in brain tissue, DNA encoding the mutant ABriPP or ADanPP, and a transcriptional and translational termination region functional in the host animal. One or more introns also can be present.

The transcriptional initiation region can be endogenous to the host animal or foreign or exogenous to the host animal. By foreign is intended that the particular region is not found in the wild-type animal into which the transcriptional initiation region is introduced. By endogenous, is intended sequences both indigenous to the host and sequences that entered the host animal as a result of a natural infection, e.g., with a virus, prion, and the like.

A promoter from a gene expressed in brain tissue of the host animal is employed for varying the phenotype of the host animal. The transcriptional level should be sufficient to provide an amount of RNA capable of production in a modified animal (an animal having a detectably different phenotype from a non-transformed animal of the same species, for example, one not having the transcriptional cassette including ABriPP or ADanPP coding sequences in its genome.

The promoter preferably comprises a transcriptional initiation regulatory region and translational initiation regulatory region of untranslated 5' sequences, "ribosome binding sites" responsible for binding mRNA to ribosomes and translational initiation. The transcriptional initiation regulatory region may be composed of cis-acting subdomains which activate or repress transcription in response to binding of transacting factors present in varying amounts in different cells. It is preferred that all of the transcriptional and translational functional elements of the initiation control region are derived from or obtainable from the same gene. In some embodiments, the promoter is modified by the addition of sequences, such as enhancers, or deletions of non-essential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

Tissue-specific transcription suggests that gene regulatory proteins are bound to enhancer sequences and other upstream promoter elements. By enhancer element ("enhancer") is intended a regulatory DNA sequence that is capable of activating transcription from a promoter linked to it, with synthesis beginning at the normal RNA start site; which is capable of operating in both orientations (normal or flipped); and which functions even when moved either upstream or downstream from the promoter. Both enhancers and other upstream promoter elements are bound by sequence-specific DNA binding proteins that mediate their effects. To identify the exact nucleotide sequences important for the function of the enhancer(s), and other upstream elements, fragments of the untranslated 5'-region encoding a protein expressed in a tissue of interest are screened for their capacity to bind nuclear proteins and for their ability to function with a heterologous promoter. Binding experiments with nuclear proteins from brain tissue can be used to determine the presence of enhancer and silencer sequences; the protein binding studies can be used to pinpoint specific nucleotide sequences that bind to a corresponding series of gene regulatory proteins.

Each enhancer and other upstream promoter elements generally is present on a segment of DNA which may contain binding sites for multiple proteins. The binding sites can generally be dissected by preparing smaller mutated versions of the enhancer sequence joined to a reporter gene whose product is easily measured. The effect of each mutation on transcription can then be tested. Alternatively, fragments of this region can be prepared. Each of the mutated versions of the enhancer sequence or the fragments can be introduced into an appropriate host cell and the efficiency of expression of a reporter gene measured. Those nucleotides required for enhancer function in this test are then identified as binding sites for specific proteins by means of gel mobility shift assays and DNA foot printing assays both routine in the art.

An alternate means of examining the capability of isolated fragments of the region upstream of the promoter to enhance expression is to look for sub-domains of the upstream region that are able to enhance expression levels from a test promoter which comprises the TATA CAAT box but shows little or no detectable activity. A fragment of the 5' region is inserted in front of the test promoter in an expression cassette, and the effect on expression of the reporter gene evaluated. Of particular interest for brain-specific, copy number-dependent expression are regions capable of binding to nuclear proteins in the region up to about 20 kb from the mRNA start site of a brain-specific protein gene. Within this region, there may be several sub-domains of interest having the characteristics of brain specific enhancer elements which can be evaluated by using constructs.

For the present invention, preferred promoters are those which provide for preferential expression in brain as compared to other tissue, preferably greater than about 10 fold compared to other tissue. Preferably, the promoter is a strong promoter which drives a high level of expression of the coding sequence in brain tissue and/or which provides for many copies of the coding sequence in brain tissue.

Any of a number of brain-specific promoters can be used, as is disclosed below. These promoters or other useful promoters known to those skilled in the art can be linked to the DNA sequences to be expressed.

(1) SM 22α (Moessler et al., *Development* 122:2415–2425 (1996)), in a pBluescript II KS vector with an SV40 polyadenylation signal.
(2) TIE2 (Schlaeger et al., *Proc. Natl. Acad. Sci. USA* 94:3058–3063 (1997)), in a pbluescript II SK vector with an SV40 polyadenylation signal
(3) Thy-1 (Lüithi et al., *J. Neurosc.*, 17:4688–4699 (1997)) in a pTSC21k vector with an SV40 polyadenylation signal. This is similar to the promoter disclosed by Moechas et al., *J. Biol. Chem.* 274:6483–6492 (1999) and by Andra et al., *Neurobiol. Aging* 17:183–190 (1996).
(4) Prion Promoter (Basler, et al. (1986), *Cell* 46:417–428 and Scott, et al. (1992) *Protein Science* 1:986–987) in a cos SyHam-TET vector with an SV40 polyadenylation signal. See, also: K. Hsiao, U.S. Pat. No. 5,877,399. Prion protein is implicated in the pathogenesis and transmission of Gerstmann-Straussler syndrome in humans and in scrapie, an equivalent non-human animal disease. Brain tissue serves as a source for nucleic acid for preparing the desired sequences. To identify a prion promoter having the desired characteristics, where a prion protein has been or is isolated, it is partially sequenced, so that a probe can be designed for identifying mRNA specific for prion protein. Sequences which hybridize to the cDNA are isolated, manipulated, and the 5' untranslated region associated with the coding region isolated and used in expression constructs to identify the transcriptional activity of the 5'-untranslated region. As appropriate, sequences can be amplified using PCR procedures known to those skilled in the art. In some instances, a probe is employed directly for screening a genomic library and identifying sequences which hybridize to the probe. The sequences will be manipulated as described above to identify untranslated region.

Other promoters known in the art to have different strengths and differing brain-or brain substructure-specificity may be substituted. A key requirement is that the promoter function in the nonhuman host being rendered transgenic, preferably a mouse. It is also desirable in some embodiments that the promoter drive expression of the transgene in a developmental pattern or cell type-specific pattern (and at expression levels) similar to a naturally-occurring BriPP gene in that host species being modified. Other useful promoters are:
(1) Neurofilament M or L promoters. These promoters demonstrate a high level of expression and are found in connection with the most abundant neural protein. They are characterized by central nervous system (CNS) and peripheral nervous system (PNS) neuronal-specific expression and have been used in connection with transgenic expression. The mouse gene promoter is published and this promoter is isolated using routine methods for use in connection with the present invention.
(2) Glial fibrillary acidic protein (GFAP) promoter sequences. Such promoters are characterized by murine specificity and CNS/PNS glial-specific expression. The promoter has been characterized and is available.
(3) Growth associated protein 43 (GAP 43) is also characterized by CNS/PNS 5neuronal-specific expression. The promoter is expressed developmentally and upon induced injury. The promoter within a rat has been characterized and is available.
(4) Nerve growth factor (NGF) promoters are characterized by PNS developmental expression and CNS maintained expression in the hippocampus and cortex which are areas afflicted by FBD and FDD. The mouse gene promoter is published and this promoter is isolated using routine methods for use in connection with the present invention.
(5) The JC Virus T antigen can be used. The human papilloma virus has neuronal tropism. The TAg promoter is characterized and is available.
(6) $pp60^{c-src}$ demonstrates 10-fold higher expression levels in CNS compared to non-neuronal cells. The regions of CNS expression are confined to specific brain regions and the promoter has been characterized.
(7) N-CAM-Neural cell adhesion molecule demonstrates murine neuronal-specific expression.

If high transgene expression leads to lethal effects that occur in the embryonic stages or early in life, such animals would not be as useful for the utilities described herein. To temper expression of the transgene, a weak promoter may be preferable. An example is the dystrophin promoter (Boyce et al., *Proc. Natl. Acad. Sci. USA* 88:1276–1280, 1991)

Other promoter sequences can be used to control expression of ABriPP or ADanPP coding sequences include the inducible metallothionine (MT) promoter from which expression can be regulated through modulation of zinc and glucocorticoid hormone levels (Palmiter, et al., *Nature* 300, 611–615 (1982)); the rat neuron specific enolase gene promoter (Forss-Petter, et al., *Neuron* 5; 197–197 (1990)); the human β actin gene promoter (Ray, et al., *Genes and Development* (1991) 5:2265–2273); the human platelet derived growth factor B chain (PDGF-B) gene promoter (Sasahara, et al., *Cell* (1991) 64:217–227); the rat sodium channel promoter (Maue, et al., *Neuron* (1990) 4:223–231); the human copper-zinc superoxide dismutase promoter (Ceballos-Picot, et al., *Brain Res.* (1991) 552:198–214); and promoters for members of the mammalian POU-domain regulatory gene family (Xi et al., (1989) *Nature* 340:35–42). The POU-domain is the region of similarity between the four mammalian transcription factors Pit-1, Oct-1, Oct-2, and unc-86, and represents a portion of the DNA-binding domain. These promoters provide for expression specifically within the neurons of transgenic animals.

For comparison and control purposes, the wild-type BriPP gene operatively linked to the same promoter and other expression control sequences is used for preparing "control transgenic animals.

The termination region which is employed primarily will be one of convenience, since the termination regions appear to be relatively interchangeable. The termination region may be native to the transcriptional initiation region, may be native to the human, or may be derived from another source. Convenient termination regions are available from the prion protein gene.

The expression cassette which is used herein includes promoter and enhancer sequences from a gene which is expressed in the brain and preferably which is expressed in a manner that is related to the number of such sequences incorporated into the chromosome, namely that higher transcription occurs with a larger number of incorporated transgene copies, operably joined to a mutant ABriPP or ADanPP gene sequence and translational and transcriptional termination regions.

As an example of construction of a cosmid vector for use in this invention, components which are assembled, in the 5' to 3' direction, include promoter and enhancer sequences of the prion protein gene, the coding sequence, and transcriptional and translational termination sequences operably attached to a cosmid vector for delivery of the DNA constructs into the pronuclei of mouse eggs for expression of the ABriPP or ADanPP gene in brain tissue. The enhancer sequences may include a 20 kb region upstream of the prion protein promoter and may also include the noncoding exon 1 and the 10 kb intron downstream of exon 1 from the prion protein gene or can include the coding sequence for more than one protein as described in, for example, WO92/11276. Using molecular genetic techniques well known in the art, the promoter/enhancer region of the prion protein gene may be isolated from a mammalian genomic cosmid clone used to create transgenic mice which express prion protein. The coding sequence is inserted between the promoter/enhancer region and the termination sequences at a unique restriction site or sites such that the coding sequence is translated in frame. A mutant BriPP protein in transgenic brain tissue introduced using a cosmid vector as described above may be confirmed to be at least two to four-fold that of endogenous levels of the animal (e.g., mouse) homologue of BriPP.

In studies designed to create an animal model of AD, a major obstacle has been the inability to overexpress transgenic amyloid precursor protein in the brain of the transgenic animal. In some cases, mRNA is expressed well, but the protein is poorly expressed. This indicates that the strength of promoters used may be adequate, but that protein translation may not be optimal. Poor translation may result from a weak translation initiation sequence. Accordingly, it may be preferred to include a translation initiation sequence wherein the positions at minus three and plus four relative to the initiation codon are A and G, respectively.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500–1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Synthetic oligonucleotides are prepared by either the phosphotriester method as described by Edge, et al., *Nature* (supra) and Duckworth, et al., *Nucleic Acids Res* (1981) 9:1691 or the phosphoramidite method as described by Beaucage, S. L., and Caruthers, M. H., *Tet Lett* (1981) 22:1859; and Matteucci, M. D., and Caruthers, M. H., *J Am Chem Soc* (1981) 103:3185 and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mMMgCl$_2$, 5 mM dithiothreitol, 1–2 mM ATP, 1.7 pmoles $\gamma$-$^{32}$P-ATP (2.9 mCi/mmole), 0.1 mM spermidine, 0.1 mM EDTA.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 0.1–1.0 mM dNTPs. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted with phenol/chloroform and ethanol precipitated. Treatment under appropriate conditions with S1 nuclease or BAL-31 results in hydrolysis of any single-stranded portion.

Ligations are performed in 15–50 ml volumes under the following standard conditions and temperatures: for example, 20 mM Tris-HCl pH 7.5, 10 mMMgCl$_2$, 10 mM DTT, 33 µg/ml BSA, 10–50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations are performed at 1 mM total ends concentration.

In vector construction employing "vector fragments", the vector fragment is commonly treated with bacterial alkaline phosphatase (BAP) or calf intestinal alkaline phosphatase (CIAP) in order to remove the 5' phosphate and prevent self-ligation of the vector. Digestions are conducted at pH 8 in approximately 10 mM Tris-HCl, 1 mM EDTA using about 1 unit of BAP or CIAP per mg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion and separation of the unwanted fragments.

For portions of vectors derived from cDNA or genomic DNA which require sequence modifications, site specific primer directed mutagenesis may be used (Zoller, M. J., and Smith, M. *Nucleic Acids Res* (1982) 10:6487–6500 and Adelman, J. P., et al., *DNA* (1983) 2:183–193). This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting partially or fully double-stranded DNA is transformed into a phage-supporting host bacterium. Cultures of the transformed bacteria are plated in top agar, permitting plaque formation from single cells which harbor the phage. Theoretically, 50% of the new plaques will contain the phage having, as a single strand, the mutated form; 50% will have the original sequence. The resulting plaques are washed after hybridization with kinased synthetic primer at a wash temperature which permits binding of an exact match, but at which the mismatches with the original strand are sufficient to prevent binding. Plaques which hybridize with the probe are then picked, cultured, and the DNA recovered.

Correct ligations for plasmid construction are confirmed by first transforming *E. coli* strain MC1061 (Casadaban, M., et al., *J Mol Biol* (1980) 138:179–207) or other suitable host with the ligation mixture. Successful transformants are selected by ampicillin-, tetracycline- or other antibiotic resistance or using other markers depending on the mode of plasmid construction, as is understood in the art. Plasmids from the transformants are then prepared according to the method of Clewell, D. B., et al., *Proc Natl Acad Sci* (USA) (1969) 62:1159, optionally following chloramphenicol amplification (Clewell, D. B., *J Bacteriol* (1972) 110:667). Several mini DNA preps are commonly used, e.g., Holmes, D. S., et al., *Anal Biochem* (1981) 114:193–197 and Birnboim, H. C., et al., *Nucleic Acids Res* (1979) 7:1513–1523. The isolated DNA is analyzed by restriction and/or sequenced by the dideoxy nucleotide method of Sanger, F., et al., *Proc Natl Acad Sci* (USA) (1977) 74:5463 as further described by Messing, et al., *Nucleic Acids Res* (1981) 9:309, or by the method of Maxam, et al., *Methods in Enzymology* (1980) 65:499.

Transgenic Animals

A number of references describe production of transgenic animals harboring and expressing human genes associated with AD or other similar neurodegenerative diseases. These documents and the documents cited therein, that instructive for the present invention, include: U.S. Pat. No. 5,387,742, U.S. Pat. No. 5,612,486, U.S. Pat. No. 5,811,633, U.S. Pat. No. 5,849,999 and U.S. Pat. No. 5,877,399.

General references for the techniques of manipulating cells and embryos, etc. can be found in: *A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987); Zjilstra et al., *Nature* 342:435–438 (1989); and Schwartzberg et al., *Science* 246:799–803 (1989), each of which is incorporated herein by reference).

The animals used as a source of fertilized eggs cells or embryonic stem cells, the "host animal", can be any animal, although the preferred host animal is one that lends itself to multigenerational studies. Other preferred characteristics of the host animal include that it is naturally able to perform the relevant cognitive tests, and that it does not die at such an early age when it expresses high levels of the mutant precursor protein of this invention that there is insufficient time for observable behavioral and/or pathological changes to occur. Of particular interest are rodents, especially mice. Examples of mouse strains that may be used include the FVD strain and crossed commercially available strains such as the (C57B1/6×SJL)$F_1$ hybrid and the (C57B1/6×DBA/2 $F_1$) hybrid (abbreviated B6D2). Mice of the $F_2$ generation of crossed $F_1$ mice may be used. Outcrosses of an $F_1$ with another strain, for example Swiss Webster×B6D2$F_1$ are useful as well. Various of the other strains and interstrain $F_1$ hybrids can be evaluated using the techniques described herein for suitability for use as a model for progressive degenerative neurologic diseases. In some instances, however, a primate, for example, a rhesus monkey may be desirable as the host animal, particularly for therapeutic testing.

Transgenic mammals are prepared in a number of ways. A transgenic organism has at least one extra or exogenous DNA fragment in its genome. In order to achieve stable replication of the exogenous DNA, an integration event must occur in a cell type that can give rise to functional germ cells, either spermatozoa or oocytes. Two cell types into which DNA can be readily introduced and that can form germ cells are (1) fertilized egg cells and (2) embryonic stem (ES) cells. ES cells can be returned from cell culture to a "host" embryo where they become incorporated into the developing animal and can give rise to transgenic cell lineages in all tissues, including germ cells. The ES cells are transfected in culture and the mutation is transmitted into the germline by injecting the cells into an embryo. Animals carrying mutated germ cells are then bred among themselves to produce transgenic offspring.

For more details regarding the production of transgenic organisms, and specifically transgenic mice, refer to U.S. Pat. No. 4,873,191 incorporated herein by reference that discloses methods for producing transgenic mice) and to the numerous scientific publications referred to and cited therein. A preferred method for making the subject transgenic animals is by zygote injection. This method is described, for example, in U.S. Pat. No. 4,736,866. The method involves injecting DNA into a fertilized egg, or zygote, and implanting the egg into in a pseudo-pregnant female and allowing it to develop. The zygote can be obtained using male or female animals of the same strain or from male or females of a different strain. The first transgenic animal that is born is called a founder, and it is bred to produce more animals carrying the same transgene. In this method of making transgenic animals, the new DNA typically integrates in a random fashion in the genome by a non-homologous recombination event. One to many thousands of copies of the DNA may integrate at a site in the genome.

Generally, the DNA is injected into one of the embryonic pronuclei, usually the larger male pronucleus. The zygotes are then either transferred the same day, or cultured overnight to form 2-cell embryos and then transferred into the oviducts of pseudo-pregnant females. The animals born from these pregnancies are screened for the presence of the desired transgene (integrated DNA).

(A pseudo-pregnant female is a female in estrus that has mated with a vasectomized male; she is competent to receive embryos but does not contain any fertilized eggs.) Pseudo-pregnant females are important for creating transgenic mice as they are surrogate mothers for the embryos that have received either the transgene DNA or the transduced ES cells.

Putative founder animals are screened for presence of the transgene in several ways. Brain ABriPP or ADanPP protein and RNA expression are analyzed at the weanling stage (4–5 weeks of age) for transgene copy number and/or level of expression using methods known to those of skill in the art. When a constitutive promoter such as the prion protein is used, changes in levels of transgenic RNA expression are not expected in animals beyond weanling age. When a developmentally-specific and/or tissue-specific promoter is used, the precursor protein levels are monitored to determine changes in expression with age. The transgenic animals also are observed for neurological, neuropathological and behavioral changes. Examples of neurobehavioral disorders for evaluation are poor mating response, agitation, diminished exploratory behavior in a novel setting, inactivity, seizures and premature death.

The founder animals can be used to produce stable lines of transgenic animals that superexpress the human BriPP gene, either mutant or wild-type. For ease of propagation, male founder mice are preferred. The animals are observed for "clinical" changes. Analyses of transgene copy number (to exclude multiple transgene insertion sites), mRNA expression, protein expression, neuropathology, and glucose uptake may be performed. The observations provide information about the age of onset of illness, the duration of illness, the penetrance of the phenotype, the range of neuropathologic findings, regional brain dysfunction, and the dependence of phenotype upon levels of protein expression. Various changes in phenotype are of interest. These changes may include progressive neurologic disease with pathological changes in cortico-limbic and cerebellar areas, vessel walls, retina and auditory regions (ear and brain), expressed within a short period of the time from birth; increased levels of expression of the ABriPP or ADanPP gene above endogenous expression levels and the development of a neurologic illness accompanied by premature death; non-neuritic plaque formation (similar to those seen in an AD variant described by Crook, R et al., *Nature Med.* 4:452–455 (1998)), neurofibrillary tangles, intracellular amyloid accretions present in the hippocampus, cerebral cortex, cerebellum and vasculature; progressive neurologic disease characterized by diminished exploratory/locomotor behavior, impaired performance on memory and learning tests, loss of vision and hearing (in the case of the ADanPP mutation) and diminished 2-deoxyglucose uptake/utilization and hypertrophic gliosis in the cortico-limbic regions of the brain and the cerebellum. Observations are also made of amyloid deposition elsewhere in the body.

The animals also are screened using species-appropriate neurobehavioral tests. For example, studies of locomotor/exploratory behavior in mice is a standard measure of neuropsychology (File and Wardill, (1975) *Psychopharmacologia* (Berl) 44:53–59; Loggi et al., (1991) *Pharmacol. Biochem. Behav.* 38:817–822). For example, the "corner index" (CI) is a quick, simple test to screen for evidence of brain pathology. A low CI (4) correlates with high mutant APP transgene copy numbers, premature death, and neuropathologic findings. The CI exhibits a dosage-dependent relationship to transgene copy number, which supports the validity of its use in assessing neurobehavioral status of the transgenic mice. With rats, the Morris water maze test (Morris, (1984) *J. Neurosci. Meth.* 11:47) is used. (A modified version can be used with mice.)

Neuropathological studies of the animals are also performed with particular attention to those brain regions known to be affected by the human syndrome of interest.

In short-lived strains of animals (either naturally or due to high expression of the mutant precursor protein PP), not all behavioral and/or pathological changes associated with the human diseases may be observed. (For example, in an AD model, transgenic FVB/N mice expressed high levels of amyloid precursor protein but tended not to develop detectable Aβ plaques, whereas longer lived C57B6/xSJL $F_1$ mice expressing identical transgenes did develop amyloid plaques which were readily detected with thioflavin S and Congo red staining.

Transgene products expressed in various brain regions are also detected using immunological or immunochemical means, for example with the antibodies disclosed herein, or mAbs specific for the appropriate ABri or ADan epitopes.

Research And Screening Uses of Transgenic Animals

Nonhuman animals comprising transgenes which encode mutant ABriPP or ADanPP (and thus ABri or ADan) can be used commercially to screen for agents having the effect of lowering amyloid production and/or accumulation. Such agents can be developed as pharmaceuticals for treating abnormal precursor protein processing and/or FBD, FDD, or other neurodegenerative conditions. For example, the p53 knockout mice of Donehower et al. (1992) *Nature* 356:215 have found wide acceptance as commercial products for carcinogen screening and the like. The transgenic animals can also be used to develop agents that modulate the precursor protein or amyloid peptide expression and/or stability; such agents can serve as drugs to treat neurodegenerative diseases. Other types of testing with the animals of this invention are discussed below.

The transgenic animals of this invention are used as test animals for agents of interest, e.g., antioxidants, that may confer protection against the development of the human diseases. An animal is treated with the test agent, and a reduced incidence or delayed onset of neurologic disease and/or neuropathological signs, as compared to untreated animals, is indicative of neuroprotection. The indices used preferably are those which can be obtained in a live animal, such as changes in performance on learning and memory tests. The effectiveness of the test agents are confirmed by their effects on neuropathology performed upon natural death or sacrifice of the animals.

The animals further can be used as models to test drugs that are capable of improving or curing dementias, neurodegenerative diseases, or in the case of the ADan mutant, hearing and vision disorders. Animals expressing the neurologic disorder are treated with compounds being screened, whereas control animals receive no treatment or appropriate control agents (e.g., placebo). Outcomes such as prolongation of life, improvement in neurobehavioral performance, gliosis, or glucose uptake/utilization are indicative of amelioration or cure.

The animals of the invention may also be used to test an agent or treatment, e.g., oxidants or head trauma, that are suspected to accelerate or exacerbate a neurodegenerative disease associated with dementia. The animals are exposed to the agent or treatment and the aforementioned behavioral or neuropathologic measures are taken. Neurobehavioral decline, premature death, gliosis, and diminished glucose uptake/utilization are indicative of the capacity of the test agent or treatment to induce or exacerbate the disease. This model is also useful for testing drugs or other therapies that may counter the effect of the above exacerbating agents or treatments.

Careful characterization of the transgenic animals will assist in elucidating the pathophysiology of progressive neurologic/neurodegenerative syndromes associated with dementia or other symptoms of FBD and FDD.

The sequence of molecular events in the metabolism of the mutant ABriPP and ADanPP leading to disease can be studied. The animals also are useful for testing additional hypotheses about pathogenesis (mostly in the context of AD disease but also relevant to FBD and FDD) including horizontal transmission (Prusiner, et al. (1987) *Cell* 63, 673–86), oxidation and free-radical production (Blass and Gibson, (1991) *Rev. Neurol* (Paris) 147:513–525; Ames et al., (1993) *Proc. Nat'l. Acad. Sci. U.S.A.* 90:7915–7922), inflammation (McGeer et al. (1993) *Can. J. Neurol. Sci.* 18:376–379, Rogers et al. (1992) *Proc. Nat'l. Acad. Sci.*

U.S.A. 89:10016–10020); neurotrophic factor deprivation (Perry, (1990) *Alzheimer's Disease and Associated Disorders* 4:1–13; Hefti and Schneider, (1991) *Clinical Neuropharmacology* 1:62–76); Koliatsoess et al., (1991) *Ann. Neurol.* 30:831–840), apolipoprotein E4 metabolism (Strittmatter et al., (1993) *Proc. Nat'l. Acad. Sci. U.S.A.* 90:1977–1981), and potassium channel dysfunction (Etcheberrigaray, et al., (1993) *Proc. Nat'l. Acad. Sci. U.S.A.* 90:8209–8213). Such knowledge would lead to improved therapies for such neurologic disorders.

Diagnosis of the ABri and ADan mutations with a DNA-Based Assay

A DNA-based assay to detect the presence of the ABri and ADan mutation is carried out as described in the Examples below.

Figure 4:
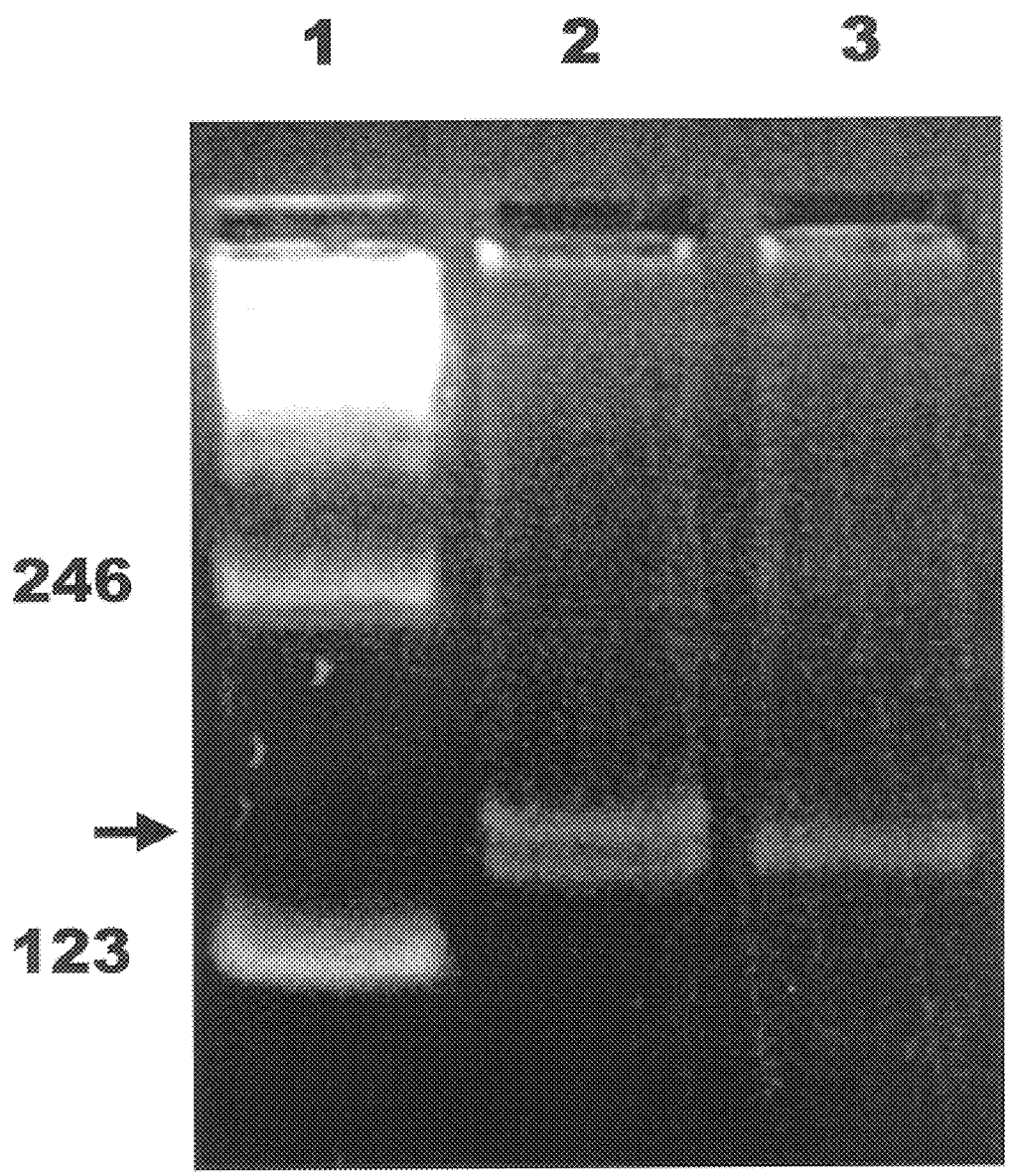
FIG. 4 shows an agarose gel electropherogram (4% Metaphor agarose gel). Lane 1: 123 molecular weight marker. Lane 2: PCR amplification of a FDD patient. Lane 3: PCR amplification of a normal control. Amplification under the same conditions using genomic DNA from a FBD patients gave identical results to normal controls. The extra band seen in FDD (151 bp) is indicated by an arrowhead.
Figure 5:
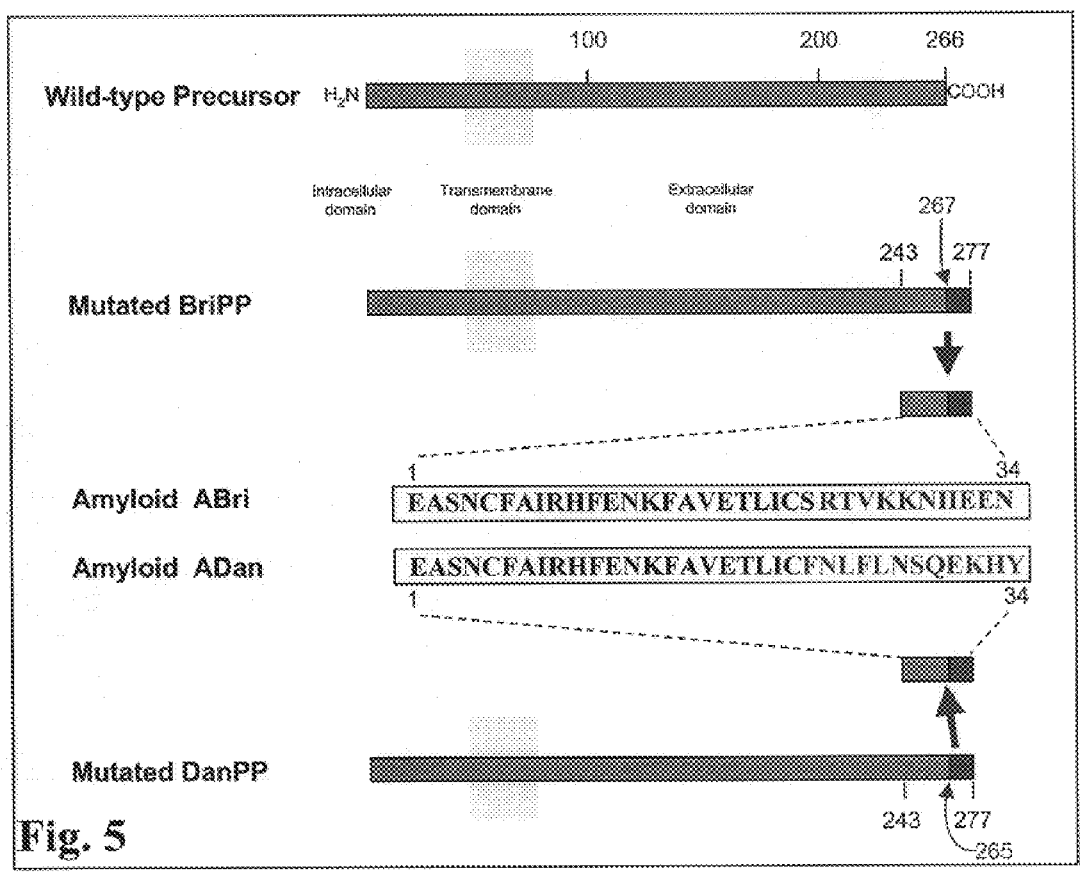
FIG. 5 is a schematic representation of the wild type amyloid precursor proteins BriPP and mutants in patients with FBD (ABriPP) and FDD (ADanPP), both of which are mutated BriPP. The topological orientation of the precursors is indicated, as well as the localization of the genetic defects in FBD and FDD. The two mutant amyloid sequences, Abri (SEQ ID NO:4) and ADan (SEQ ID NO:10) are boxed, with the putative cleavage site between codons 243 and 244 indicated. Due to the particular nature of these mutations, both amyloid peptides originate from longer mutant precursor proteins of 277 amino acids.

Th ABri mutation introduces an XbaI restriction site into-the DNA. Thus, a test DNA sample from a person suspected of having the mutation is after amplified in PCR using the primers described herein. The amplified DNA is treated with XbaI and run on an agarose gel. Because the mutations are heterozygous, an individual bearing the mutation has one normal allele and one mutant. Thus, a normal DNA sample yields a single band in this test because of the absence of an XbaI site. An ABri mutant subject's DNA yields 3 bands, one larger normal band (from the normal allele) and two smaller restriction fragments due to the mutation. A gel pattern such as the one shown in FIG. 4 is therefore diagnostic of the ABri mutation.

The ADan mutation does not introduce a restriction site. However, PCR amplification of the DNA results in two amplification products. One is a 141 bp polynucleotide corresponding to the wild-type sequence, and the second is a 151 bp polynucleotide corresponding to the mutant sequence (See FIG. 4).

Thus, a population at risk can be screened for the presence of either of the mutant alleles that are associated with FBD and FDD.

Mutant Proteins and Peptides and Their Variants

The present invention is also directed to the two mutant precursor proteins, ABriPP and ADanPP, substantially free of other proteins with which they are natively associated. Also included are all peptide fragments of the precursor protein, preferably the amyloid peptide ABri [SEQ ID NO:5 and ADan [SEQ ID NO:6 ]. Also preferred are peptides having the additional sequence present each of the two mutants but absent from wild-type BriPP. These peptides are: CTVKKNIIEEN [SEQ ID NO:11] for ABri and CFNLFLNSQEKHY [SEQ ID NO:12] for ADan, as well as longer peptides that include these sequences. Other preferred peptides are those including epitopes recognized by antibodies to the whole proteins. These proteins and peptides have a number of uses, including as antigens or immunogens for producing antibodies specific for the mutant BriPP or for assaying for such antibodies in sera of patients or in experimental animals.

Also included within the scope of this invention is a functional derivative of a mutant BriPP. By "functional derivative" is meant a "fragment," "variant," "analogue," or "chemical derivative" of the protein which terms are defined below. A functional derivative retains at least a portion of the function of BriPP which permits its utility in accordance with the present invention.

A "fragment" of the protein refers to any subset of the molecule, that is, a shorter peptide. Thus, ABri and ADan are fragments of mutant BriPP.

A "variant" of the protein or peptide refers to a molecule substantially similar to the protein or a peptide, and typically is a substitution variant, as discussed below. A variant peptide may be conveniently prepared by direct chemical synthesis using methods well-known in the art.

An "analogue" of the protein or peptide refers to a non-natural molecule substantially similar to either the entire molecule or a fragment thereof.

A "chemical derivative" of the protein or peptide contains additional chemical moieties not normally a part of the peptide (see below).

One type of variant of the proteins and peptides of this invention involves substitution of at least one amino acid residue and preferably, only one, with a different residue. For a detailed description of protein chemistry and structure, see Schulz, GE et al., *Principles of Protein Structure*, Springer-Verlag, New York, 1978, and Creighton, T. E., *Proteins: Structure and Molecular Properties*, W. H. Freeman & Co., San Francisco, 1983, which are hereby incorporated by reference. The types of substitutions which may be made in the protein or peptide molecule of the present invention may be based on analysis of the frequencies of amino acid changes between a homologous protein of different species, such as those presented in Table 1–2 of Schulz et al. (supra) and FIG. 3–9 of Creighton (supra). Based on such an analysis, conservative substitutions are defined herein as exchanges within one of the following five groups:

| | |
|---|---|
| 1. Small aliphatic, nonpolar or slightly polar residues | Ala, Ser, Thr (Pro, Gly) |
| 2. Polar, negatively charged residues and their amides | Asp, Asn, Glu, Gln |
| 3. Polar, positively charged residues | His, Arg, Lys |
| 4. Large aliphatic, nonpolar residues | Met, Leu, Ile, Val (Cys) |
| 5. Large aromatic residues | Phe, Tyr, Trp |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation which is important in protein folding. (Schulz et al., supra, would merge Groups 1 and 2). Tyr (Group 5), because of its hydrogen bonding potential, has some kinship with Ser, Thr, etc. (Group 1).

More substantial changes in biochemical, functional or immunological properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most acceptable deletions and insertions, and substitutions according to the present invention are those which do not produce radical changes in the characteristics of the protein or peptide. However, when it is difficult to predict the exact effect of the substitution, deletion, or insertion in advance of doing so, one skilled in the art will appreciate that the effect can be evaluated by routine screening assays. Shorter chain variants are made by chemical synthesis. Longer chain variants are typically made by site-specific mutagenesis of the nucleic acid encoding the peptide, expression of the variant nucleic acid in cell culture, and, optionally, purification of the protein/peptide from the cell culture, for example, by immunoaffinity chromatography using specific antibody immobilized to a column (to absorb the variant by binding to at least one epitope).

The activity of a cell lysate or purified protein or peptide-variant is screened in a suitable screening assay for the desired characteristic. For example, a change in the immunological character of the protein or peptide molecule is assayed by alterations in binding to a given antibody, and is measured by a competitive immunoassay. Biological activity is screened in an appropriate bioassay, as described below. When appropriate, measurement of receptor-ligand binding is a way to screen a variant for biochemical or functional properties.

Modifications of peptide properties such as redox or thermal stability, hydrophobicity, susceptibility to proteolytic degradation or the tendency to aggregate with carriers or into multimers are assayed by methods well known to the ordinarily skilled artisan.

Chemical Modifications of the Peptides

The present invention also includes a "chemical derivative" of the mutant ABriPP. Covalent modifications may be introduced by reacting targeted amino acid residues of the peptide with an organic derivatizing agent that is capable of reacting with selected side chains or terminal residues.

Cysteinyl residues most commonly are reacted with α-haloacetates (and corresponding amines) to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alcylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate (pH 5.5–7.0) which agent is relatively specific for the histidyl side chain. p-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents reverses the charge of the lysinyl residues. Other suitable reagents for derivatizing ac-amino-containing residues include imidoesters such as methylpicolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, including phenylglyoxal, 2,3-butanedione, 1,2-cyclohexanedione, and ninhydrin. Such derivatization requires that the reaction be performed in alkaline conditions because of the high $pK_a$ of the guanidine functional group. Furthermore, these reagents may react with the groups of lysine as well as the arginine ε-amino group.

Modification of tyrosyl residues has permits introduction of spectral labels into a peptide. This is accomplished by reaction with aromatic diazonium compounds or tetranitromethane. Most commonly, N-acetylimidizol and tetranitromethane are used to create O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide.

Aspartyl and glutamyl residues are converted to asparaginyl and glutaminyl residues by reaction with ammonium ions. Conversely, glutaminyl and asparaginyl residues may be deamidated to the corresponding glutamyl and aspartyl residues. Deamidation can be performed under mildly acidic conditions. Either form of these residues falls within the scope of this invention.

Derivatization with bifunctional agents is useful for cross-linking the peptide to a water-insoluble support matrix or other macromolecular carrier. Commonly used cross-linking agents include 1,1-bis(diazoacetyl)-2-phenylethane, glutaraldehyde, N-hydroxy-succinimide esters, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane.

Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other chemical modifications include hydroxylation of proline and lysine, phosphorylation of the hydroxyl groups of seryl or threonyl residues, methylation of the α-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl.

Such chemically modified and derivatized moieties may improve the peptide's solubility, absorption, biological half life, and the like. These changes may eliminate or attenuate undesirable side effects of the proteins or peptides in vivo. Moieties capable of mediating such effects are disclosed, for example, in *Remington's Pharmaceutical Sciences*, Mack Publishing Company, Easton Pa. (Gennaro 18th ed. 1990).

The present invention includes the proteins or peptides immobilized to a solid support or carrier. By "solid phase support" is intended any support capable of binding a protein or peptide in a way that permits binding to that immobilized protein or peptide of a ligand or binding partner, e.g., an antibody. Well-known supports, or carriers, include glass, a number of plastics including polystyrene, polypropylene and polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Antibodies Specific for Mutant Amyloid Proteins

Using the ABriPP and ADanPP polypeptides, it is possible to prepare antisera and mAbs). Such monoclonal antibodies could then form the basis of a diagnostic test for the presence of the British or the Danish mutation in humans, among other uses. As described below, such antibodies or derivatives thereof (e.g., single chain antibodies) are useful as therapeutic agents.

The mutant precursor protein or peptides may be used to immunize an animal for the production of specific antibodies. Formulations for immunization are discussed the "vaccine" sections below. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, N.Y., which is incorporated herein by reference.

For example, a recombinantly produced fragment of ABriPP can be injected into a mouse or rabbit along with an adjuvant to induce an immune response. Murine or rabbit immunoglobulins which bind the recombinant fragment with a pre-selected binding affinity, e.g., at least $1 \times 10^7$ M$^{-1}$ can be harvested from the immunized animals as an antiserum, and may be further purified by affinity chromatography or other means. Additionally, spleen cells are harvested from an immunized mouse and fused to myeloma cells to produce a bank of antibody-secreting hybridoma cells which are screened for clones that secrete immunoglobulins having the desired properties, e.g., bind the recombinantly produced fragment with an affinity of at least $1 \times 10^6$ M$^{-1}$. Antibodies that bind to the mutant precursor protein but have limited crossreactivity with a wild-type BriPP are selected, either by preabsorption with wild-type BriPP or by screening of hybridoma cell lines for specific idiotypes that preferentially bind the mutant as compared to the wild-type.

Such antibodies will recognize amyloid deposits in FBD and FDD patients. An anti-ABri polyclonal rabbit antibody was made by immunization of animals with a synthetic peptide CTVKKNIIEEN [SEQ ID NO:11] corresponding to the 10 C-terminal residues of the ABri peptide with an extra N-terminal Cys residue. Addition of this Cys permitted efficient coupling or conjugation of the peptide to an immunogenic carrier protein, e.g., keyhole limpet hemocyanin.

Another anti-ABri polyclonal antibody preparation was made by immunizing rabbits with purified ABri amyloid of the sequence

EASNCFAIRHFENKFAVETLICSRTVKKNIIEEN [SEQ ID NO:13].

An anti-ADan polyclonal antibody was made by immunization with a synthetic peptide homologous to the 13 C-terminal residues of the ADan, having the sequence CFNLFLNSQEKHY [SEQ ID NO:12].

Immunoassay of Amyloid Precursor Protein or Peptide or their Antibodies

Antibodies (or the proteins or peptides are preferably tested or detected in an enzyme immunoassay (EIA), or enzyme-linked immunosorbent assay (ELISA). Such assays are described in greater detail in: Butler, J. E., The Behavior of Antigens and Antibodies Immobilized on a Solid Phase (Chapter 11) In: *STRUCTURE OF ANTIGENS*, Vol. 1 (Van Regenmortel, M., CRC Press, Boca Raton 1992, pp. 209–259; Butler, J. E., ELISA (Chapter 29), In: van Oss, C. J. et al., (eds), *Immunochemistry*, Marcel Dekker, Inc., New York, 1994, pp. 759–803 Butler, J. E. (ed.), *Immunochemistry of Solid-Phase Immunoassay*, CRC Press, Boca Raton, 1991; Voller, A. et al., *Bull. WHO* 53:55–65 (1976); Voller, A. et al., *J. Clin. Pathol.* 31:507–520 (1978); Butler, J. E., Meth. Enzymol. 73:482–523 (1981); Maggio, E. (ed.), *Enzyme Immunoassay*, CRC Press, Boca Raton, 1980 Ishikawa, E. et al. (eds.) *Enzyme Immunoassay*, Kgaku Shoin, Tokyo, 1981.

In these assays, an enzyme is coupled to the antibody, the antigen, or preferably, to a second antibody that binds either to the antigen (i.e., peptide of the invention) or to an antiglobulin antibody that binds to the anti-peptide antibody. When exposed to a substrate, the enzyme will react with the substrate to produce a chemical moiety detectable by, for example, spectrophotometric, fluorometric or by visual means. Enzymes which can be used in this assay include, but are not limited to, horseradish peroxidase, alkaline phosphatase, glucose-6-phosphate dehydrogenase, malate dehydrogenase, staphylococcal nuclease, Δ-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucoamylase and acetylcholinesterase.

Useful immunoassays include sandwich assays as well as competitive assays, both well-known in the art.

A radioimmunoassay (RIA) utilizes a radiolabeled antibody, antigen or second antibody (Weintraub, B., *Principles of Radioimmunoassays*, Seventh Training Course on Radioligand Assay Techniques, The Endocrine Society, March, 1986; Work, T. S. et al., *Laboratory Techniques in and biochemistry and Molecular Biology*, North Holland Publishing Company, New York, (1978), chapter: Chard, T., "An Introduction to Radioimmune Assay and Related Techniques." The radioisotope can be detected by gamma counter, scintillation counter or autoradiography. Isotopes which are particularly useful for this purpose are: $^3$H, $^{125}$I, $^{131}$I, $^{35}$S, $^{14}$C and preferably $^{125}$I.

An antibody may be labeled with a fluorescent compound. When the fluorescently labeled antibody is exposed to light of the proper wave length, its presence can be detected due to fluorescence. Among the most commonly used fluorophores are fluorescein isothiocyanate, rhodamine, phycoerythrin, phycocyanin, allophycocyanin, o-phthaldehyde and fluorescamine. Alternatively, the antibody can be detectably labeled with fluorescence emitting metals such as $^{152}$Eu, or others of the lanthanide series. These metals can be attached to an antibody using metal chelating groups such as diethylenetriaminepentaacetic acid (DTPA) or ethylenediaminetetraacetic acid (EDTA).

The antibody can be detectably labeled by coupling it to a chemiluminescent compound. The presence of the chemiluminescent-tagged antibody is then determined by measuring luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibody of the present invention, for example, luciferin, luciferase or aequorin.

In situ detection of the peptide (or the antibody) in a tissue or cell preparation may be accomplished by removing a histological specimen from a subject, and incubating with the appropriately labeled antibody (or peptide) to such a specimen. Such procedures allow determination not only the presence of the binding partner (peptide or antibody) but also its distribution in the examined tissue. Using the present invention, those of ordinary skill will readily perceive that any of a wide variety of histological methods (such as staining procedures) can be modified in order to achieve such in situ detection.

The latter method is particularly useful for testing brain tissue samples, e.g., postmortem samples in subjects or in transgenic animal models. This is exemplified below. See, in particular, FIG. 4.

Diagnosis with DNA-Based Assays

A DNA-based assay to detect the presence of the ABri and ADan mutation is carried out as described in the Examples below.

The ABri mutation introduces an XbaI restriction site into the DNA. Thus, a test DNA sample from a person suspected of having the mutation is after amplified in PCR using the primers described herein. The amplified DNA is treated with XbaI and run on an agarose gel. Because the mutations are heterozygous, an individual bearing the mutation has one normal allele and one mutant. Thus, a normal DNA sample yields a single band in this test because of the absence of an XbaI site. An ABri mutant subject's DNA yields 3 bands, one larger normal band (from the normal allele) and two smaller restriction fragments due to the mutation. A gel pattern such as the one shown in FIG. 7A is therefore diagnostic of the ABri mutation.

The ADan mutation does not introduce a restriction site. However, PCR amplification of the DNA results in two amplification products. One is a 141 bp polynucleotide corresponding to the wild-type sequence, and the second is a 151 bp polynucleotide corresponding to the mutant sequence.

Immunological Approaches in the Therapy of FBD and FDD

The present invention is directed to methods for treating FBD and FDD, or for alleviating symptoms associated with these disease states that involve induction of immune responses to epitopes of the mutant amyloid proteins. While the mechanism of this approach is not yet resolved, it may involve the actions of antibodies in conjunction with accessory cells such as microglia in the brain, or with T cell mediated immunity. The present embodiments are not limited by any particular immune mechanism that underlies the desired effects.

D. Schenk et al. (*Nature* 400:173–177 (1999)) recently described an initial study in transgenic mice which had been developed as an animal model to test potential treatments for Alzheimer's disease. See commentary by Blass, New Eng J Med, 1999-341:1694–1695 and Duff, K., Trends Neurosci November 1999 ;22(11):485–486. The transgenic mice overexpress a mutant form of the human amyloid precursor protein (APP). The cerebral amyloidosis that develops in these animals is similar to that in the brains of patients with Alzheimer's disease. Cerebral amyloidosis was largely prevented in animals that were immunized with a fragment of APP, namely, Aβ1-42, at the age of 6 wks, before amyloid began to accumulate in their brains.

Immunization of 11-month-old mice, after amyloid began to be deposited in the brain, reduced the amount of cerebral amyloidosis expected with aging, as evidenced by examination of their brains 7 months later. Because they carry the mutant human gene in their genome, the transgenic animals might be expected to recognize the amino acid sequence of the protein as "self". It was speculated that the protein fragment used for immunization may fold in a way that creates an antigenic surface that the immune system recognize as foreign.

Many workers in the field of AD have accepted the idea that the deposition of dense amyloid is the critical event, with cerebral amyloidosis leading to the brain damage that causes the signs and symptoms of the disease. This train of events has been called the amyloid-cascade hypothesis of AD. If the amyloid-cascade hypothesis of AD is correct and if immunization prevents the accumulation of amyloid in patients at risk for AD or ameliorates amyloidosis in patients with established disease, then this approach has many clinical implications. For example, in AD, immunization might lead to antibodies that react with the normal, endogenous protein that is expressed throughout the body in humans. APP is a nexin and appears to have a role in normal physiology. For example, one of its splice variants is found in high concentrations in platelets. APP knockout mice have neurologic deficits. (Seabrook G R et al., *Neuropharmacology* 38:349–59 (1999)) Therefore, immunization of humans may not be harmless. Nevertheless, immunization was not reported to be harmful to the transgenic mice in which the protein was overexpressed.

Use of this approach in FBD or FDD has the advantage that the affected subjects are heterozygotes for the mutant protein. Thus, immunization with, and an immune response specific for a mutant peptide would not be expected to interfere with function of the normal protein encoded by the nonmutant allele.

In the present invention, a subject is immunized or vaccinated with a peptide that includes the mutant portion of the amyloid peptide characteristic of the disease. In the case of ABri, the subject is immmunized with a vaccine that includes the mutant 11-mer sequence RTVKKNIIEEN [SEQ ID NO:14]. In the case of ADan, the subject should be immunized with a "vaccine" that includes the mutant 11-mer sequence FNLFLNSQEKHY [SEQ ID NO:15]. Modified peptides that can be used as immunogens include a sufficient portion of this sequence so that an immune response includes T cells or antibodies specific for at least an epitope of this mutant peptide. As indicated above, a synthetic peptide CTVKKNIIEEN (SEQ ID NO:11, described above) corresponding to the 10 C-terminal residues of the ABri peptide with an extra N-terminal Cys residue was used because addition of this Cys permitted efficient coupling or conjugation of the peptide to an immunogenic carrier protein. For the ADan peptide, a 13-mer that includes the "natural" Cys (CFNLFLNSQEKHY, SEQ ID NO:12, described above) is conveniently conjugated to a carrier through the Cys residue.

Fusion proteins between these peptides and another protein are also a suitable way in which these peptides can be rendered immunogenic and used to vaccinate a subject. This technology is well-known in the art. The fusion partner can simply act as a carrier or can include, for example, a stretch of amino acids that have immunoenhancing activity, such as a 9 residue immunoenhancing peptide from IL1-1β (Beckers, W. et al., 1993, *J. Immunol.* 151:1757–1764).

Formulation of Polypeptide or Peptide Vaccines

The protein/peptide composition that is formulated as a vaccine can be the whole target protein (ABriPP/ADanPP) or fragments thereof. A preferred vaccines includes the 11-mer mutant sequence as indicated above.

In some cases, the immunogenicity or effectiveness of the protein/peptide may benefit from its being conjugated to a suitable carrier, usually another larger protein molecule that is foreign to the host being immunized. In such a construct, multiple copies of the peptide may be conjugated to a single larger carrier molecule. The carrier may have properties which facilitate transport, binding, absorption or transfer of the polypeptide immunogen. Conjugation between proteinaceous materials is readily accomplished using conventional methods, e.g., bifunctional cross-linkers as binding agents (Means et al., *Bioconjugate Chem.* 1:2–12 (1990)). Examples of suitable carriers are the tetanus toxoid, the diphtheria toxoid, serum albumin, keyhole limpet hemocyanin and the like. Conjugates including these "universal" carriers can stimulate T cell responses (e.g., helper cells for antibody responses) in a less MHC-restricted manner than would occur without them.

The immunogenic protein/peptide may be combined or mixed with various fluids and with other substances known in the art. The polypeptide is formulated conventionally using methods well-known for formulation of such vaccines. The active ingredient is generally dissolved or suspended in an acceptable carrier such as water, saline or phosphate buffered saline.

The vaccine composition may further comprise one or more adjuvants or immunostimulating agents. Examples of adjuvants or agents that may add to the effectiveness of the protein as an immunogen include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, whole organisms or subcellular fractions of the bacteria *Propionobacterium acnes* or *Bordetella pertussis*, polyribonucleotides, sodium alginate, lanolin, lysolecithin, vitamin A, saponin and saponin derivatives (such as QS21 exemplified herein), liposomes, levamisole, DEAE-dextran, blocked copolymers or other synthetic adjuvants. Another adjuvant is ISAF-1 ((5% squalene, 2.5% pluronic L121, 0.2% Tween 80 in phosphate-buffered solution with 0.4 mg of threonyl-muramyl dipeptide). Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.), Amphigen (oil-in-water), Athydrogel (aluminum hydroxide), or a mixture of Amphigen and Alhydrogel. Aluminum is approved for human use. The vaccine material may be adsorbed to or conjugated to beads such as latex or gold beads, ISCOMs, and the like. General methods to prepare vaccines are described in Remington's Pharmaceutical Science; Mack Publishing Company Easton, Pa. (latest edition).

Liposomes are pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature. Adjuvants, including liposomes, are discussed in the following references, incorporated herein by reference: Gregoriades, G. et al., *Immunological Adjuvants and Vaccines*, Plenum Press, New York, 1989 Michalek, S. M. et al., *Curr. Top. Microbiol. Immunol.* 146:51–58 (1989).

Additional discussion of vaccine design, particularly controlled release systems, can be found in Powell, M. F. et al (eds), *Vaccine Design: The Subunit and Adjuvant Approach*, Powell, M. F. et al. (eds), Plenum Press, New York 1995, p 389–412. Controlled release systems are already used in humans as "depots" to deliver any array of drugs and hormones (Langer, R. 1990, *Science* 249: 1527–1533). Such systems may have a significant impact on immunization since they can be designed to deliver controlled amounts of antigen continuously or in spaced pulses at predetermined rates (Cohen et al., 1991, *Pharm. Res.* 8:713–720; Eldridge et al., 1991a, *Mol. Immunol.* 28:287–294; Gander et al. 1993, in: *Proc. Int. Syn. Control. Rel. Bioact. Mater.*, Controlled Release Society, Washington, D.C., pp. 65–66), while simultaneously protecting undelivered antigen from rapid degradation in vivo. Controlled release microspheres have considerable potential for oral immunization (Edelman et al., 1993, *Vaccine* 11:155–158; Eldridge et al., 1990, *J. Control. Rel.* 11:205–214; McQueen et al., 1993, *Vaccine* 11:201–206; Moldoveanu et al., 1989, *Curr Top. Microbiol. Immunol.* 146:91–99; O'Hagan et al., 1993b, *Vaccine* 11: 149–154; Reid et al. 1993, *Vaccine* 11:159–167). Other potential advantages of polymeric controlled release systems include: lower dosage requirements, leading to a decreased probability of unwanted side effects and decreased cost; localized or targeted delivery of antigen to antigen-presenting cells or the lymphatic system; more than one antigen may be encapsulated, facilitating the design of a formulation that can immunize an individual against more than one disease, or against several epitopes in a single injection; and improved patient compliance. In addition, controlled release systems may eventually reduce the number of vaccine doses required for successful vaccination to a single injection.

Microspheres may be particularly suited as controlled release vaccine carriers for two reason: (1) particles greater than 10 $\mu$m in diameter are capable of providing a long-term persistence of antigen at the site of injection which may be necessary for a sustained high-level antibody immune response and (2) microparticles in the size range of 1–10 $\mu$m are readily phagocytosed by macrophages (Eldridge et al., 1989, *Adv. Exp. Med. Biol.* 251:192202; Tabata et al., 1988, *Biomaterials* 9:356–362; *J. Biomed Mater Res.* 22:837–858) leading to direct intracellular delivery of antigen to antigen-presenting cells. Among the advantages of using polymer microspheres for vaccine delivery is the ability to control the time following administration at which the antigen is released. This capability allows the fabrication of a single-injection formulation that releases multiple "pulses" of vaccine at predetermined times following administration (Gilley et al., 1992, In: *Proc. Int. Symp. Control. Rel. Bioact. Mater*, Controlled Release Society, Orlando, pp. 110–111). Antigen release kinetics from polymer microspheres can be controlled to a great extent by the simple manipulation of such variable as polymer composition and molecular weight, the weight ratio of vaccine to polymer (i.e., the vaccine loading), and microsphere size (Hanes et al., In: *Reproductive Immunology*, 1995, R. Bronson et al., eds, Blackwell. Oxford). Vaccine formulations that contain a combination of both small (1–10 $\mu$m) and larger (20–50 $\mu$m) microspheres may produce higher and longer-lasting antibody levels compared to the administration of vaccine encapsulated in microspheres with diameters of exclusively 1–10 or 20–50 $\mu$m (Eldridge et al., 1991a, *Mol. Immunol.* 28287–294). In one study, tetanus toxoid (TT)-containing microspheres were tailored to produce a strong priming antigen dose released over the first few days after injection followed by two "boosting" doses released after 1 and 3 months, respectively, in order to mimic conventional vaccination schedules (Gander et al., supra).

The most widely used polymers for vaccine microencapsulation have been the polyesters based on lactic and glycolic acid. These polymers have several advantages, including extensive data on their in vitro and in vivo degradation rates (Lewis, 1990, In: *Biodegradable Polymers as Drug Delivery Systems* (Chasin and Langer, eds.), Dekker, New York, pp. 1–41; Tice and Tabibi, 1992, In: *Treatise on*

Controlled Drug Delivery (A. Kydonieus, ed.), Dekker, New York, pp. 315–339, and FDA approval for a number of clinical applications in humans such as surgical sutures (Gilding et al., 1979, *Polymer* 20:1459–1464; Schneider, 1972, U.S. Pat. No. 3,636,956) and a 30-day microsphere-based controlled delivery system for leuprolide acetate (Lupron Depot) used in the treatment of prostate cancer and endometriosis (Okada et al., 1991, *Pharm. Res.* 8:787–791).

The vaccine compositions preferably contain (1) an effective amount of the immunogenic polypeptide together with (2) a suitable amount of a carrier molecule or, optionally a carrier vehicle, and, if desired, (3) preservatives, buffers, and the like. Descriptions of vaccine formulations are found in Voller, A. et al., *New Trends and Developments in Vaccines*, University Park Press, Baltimore, Md. (1978).

In one embodiment, the vaccine composition includes one or more cytokines. GM-CSF is a potent immunostimulatory cytokine with efficacy in promoting T cell responses (Bendandi, M et al., (1999) *Nature Med* 5:1171–1177). In a related embodiment, proinflammatory chemokines may be added, e.g., interferon inducible protein 10 and MCP-3 (Biragyn A et al., *Nature Biotechnol.* (1999) 17:253–258). In general, it appears that any cytokine or chemokine that induces inflammatory responses, recruits antigen presenting cells (APC) and, possibly more importantly, promotes targeting of antigen presenting cells (APC) for chemokine receptor-mediated uptake of the polypeptide antigen, is useful in the present vaccine formulation.

As with all immunogenic compositions for eliciting antibodies, the immunogenically effective amounts of the proteins or peptides of the invention must be determined empirically. Factors to be considered include the immunogenicity of the native polypeptide, whether or not the polypeptide will be complexed with or covalently attached to an adjuvant or carrier protein or other carrier and the route of administration and the number of immunizing doses to be administered. Such factors are known in the vaccine art, and it is well within the skill of immunologists to make such determinations without undue experimentation. Preferably, an effective amount of the protein or polypeptide is between about 0.01 µg/kg and about 1 mg/kg body weight. The amount of the immunogen per dose can range from about 0.01 mg to 100 mg of protein per subject per injection. A preferably range is from about 0.2 to 2 mg per dose. A suitable unit dose size is about 0.5 ml. Accordingly, a unit dosage form for subcutaneous injection could comprise 0.5 mg of immunogen admixed with 0.5% aluminum hydroxide in 0.5 ml.

Administration is preferably by injection on one or multiple occasions to produce systemic immunity. In general, multiple administrations of the vaccine in a standard immunization protocol are used, as is standard in the art. For example, the vaccines can be administered at approximately two to six week intervals, preferably monthly, for a period of from one to six inoculations in order to provide protection.

The vaccine may be administered by any conventional route including oral and parenteral. Examples of parenteral routes are subcutaneous, intradermal, transcutaneous, intravenous, intramuscular, intraorbital, intracapsular, intrathecal, intraspinal, intracistemal, intraperitoneal, etc.

Vaccination with the vaccine composition will result in a systemic immune response, which includes either or both of an antibody response and a cell-mediated immune response. This should result in antibodies (see below) and activated T lymphocytes of various classes which may be used themselves as therapeutic agents. In addition such antibodies or T cells have a number of research uses that are evident to those skilled in the art.

The proportion of the protein/peptide immunogen and the adjuvant can be varied over a broad range so long as both are present in effective amounts. For example, aluminum hydroxide can be present in an amount of about 0.5% of the vaccine mixture ($Al_2O_3$ basis).

After formulation, the vaccine composition may be incorporated into a sterile container which is sealed and stored at a low temperatures, for example 4° C. or –20° C. or –80° C. Alternatively, the material may be lyophilized which permits longer-term storage in a stabilized form.

Antibodies as Therapeutic Agents in FBD and FDD

In AD, β-amyloid peptide (Aβ) accumulates in the brain as insoluble amyloid plaques. The analogous situation occurs in FBD and FDD, where ABri and ADan mutant peptides accumulate in brains (as well as in peripheral organs). Amyloid filaments, similar to those found in plaques, can be assembled in vitro from chemically synthesized β-peptides. Solomon B et al., Proc Natl Acad Sci USA 1996 93:452–455, showed that two mAbs raised against Aβ fragments spanning amino acid residues 1–28 and 8–17 of the Aβ chain, respectively prevented aggregation of Aβ in vitro. The inhibitory effect appeared related to the localization of the antibody-binding sites and the nature of the aggregating agents. MAbs against "aggregating epitopes" (sequences related to the sites where protein aggregation is initiated) will therefore assist in preventing undesired protein aggregation in vivo to prevent or attenuate the amyloid aggregation associated with FBD and FDD.

Antibodies raised against the N-terminal region Aβ1-28 bound to the in vitro-formed amyloid assemblies, leading to disaggregation of the fibrils and partial restoration of the peptides' solubility (Solomon B et al. *Proc Natl Acad Sci USA* 1997, 94:4109–4112). Addition of these antibodies along with fibrillar β-amyloid to PC 12 cells inhibited the neurotoxic effects of the amyloid. Thus, appropriate site-directed mAbs can interfere with the aggregation of β-amyloid and reverse the aggregated form to its nontoxic, normal form. The present invention thus provides a method to convert amyloid plaques in vivo into nontoxic, diffuse components, thereby having therapeutic benefit for FBD and FDD. Use of antibodies of appropriate specificity make this approach useful for treating other human diseases associated with the pathologic amyloidogenic properties of physiological peptides and proteins.

The Solomon group (Frenkel D et al., *J Neuroimmunol*, 1998, 88:85–90) localized the epitopes of two mAbs (from the above studies) using a phage library displaying random combinatorial hexapeptides. Most positive phage-clones selected from the library by both antibodies carried the consensus sequence EFRH (SEQ ID NO:24) and bound the above two mAbs specifically with a $K_d$ of about $10^{-9}$M. EFRH (SEQ ID NO: 24) inhibited binding of these mAbs to Aβ with the same affinity as did Aβ1-9, Aβ1-16 and Aβ1-40. Thus, EFRH (Aβ3-6) (SEQ ID NO:24) acts a linear epitope with these mAbs. Analogously, in the present invention, N-terminal peptides of ABri and ADan are used to screen for high affinity antibodies that bind to these mutant peptides and that will be usefull to inhibit amyloid peptide aggregation. Frenkel D et al., *J Neuroimmunol* 1999, 95:136–1342, showed that, while two mAbs (6C6 and 10D5) inhibited the formation of β-amyloid fibrils, triggered disaggregation and reversal to the non-toxic form, a third mAb (2H3) devoid of these properties bound a different epitope DAEFRHD (SEQ ID NO:25), corresponding to Aβ1-7, with high affinity similar to its affinity for the whole Aβ. While the EFRH (SEQ ID NO:24) peptide strongly inhibited binding of 6C6 and 10D5 to Aβ, it inhibited only weakly the interaction of 2H3 with Aβ. Such low affinity binding might explain the mAb's failure to prevent amyloid formation. Therefore, useful antibodies for the present therapeutic methods preferably have an affinity for ABri or ADan, or a peptide thereof, of at least $K_d \leq 10^{-7}$M, preferably $K_d \leq 10^{-8}$M and, more preferably, $K_d \leq 10^{-9}$M.

In AD, pathological effects of Aβ fibrils are confined0 to the CNS. FBD and FDD differ in that amyloid is deposited in the periphery as well. Thus, in AD, it is necessary (and in FBD and FDD it is preferable) to overcome the low permeability of the blood-brain barrier for antibodies in order for the present approach to succeed in inhibiting or reversing the brain pathology. Well-known antibody engineering methods can be used to minimize size of mAbs (135–900 kDa) while maintaining biological activity.

One engineered form of antibody is a single chain antibody also termed "scFv." This designation has its origin in the naming of the Fv fragment that arose from the fact that a dimer of the immunoglobulin (Ig) $V_H$ region and the $V_L$ region released enzymatically from an intact Ig by mild proteolysis followed by reassociation could refold properly and maintain antigen binding activity (Hochman, J. et al. (1973) Biochemistry 12:1130–1135; Sharon, J, et al.(1976) Biochemistry 15:1591–1594). These single chain polypeptides include the hypervariable regions from an antibody of interest and recreate the antigen binding site of the native Ig while being a fraction of the size of the intact Ig (Skerra, A. et al. (1988) Science, 240: 1038–1041; Pluckthun, A. et al. (1989) Methods Enzymol. 178: 497–515; Winter, G. et al. (1991) Nature, 349: 293–299); Bird et al., (1988) Science 242:423; Huston et al. (1988) Proc. Natl. Acad. Sci. USA 85:5879; U.S. Pat. Nos. 4,704,692, 4,853,871, 4,946,778, 5,260,203, 5,455,030. Ladner (U.S. Pat. No. 4,704,692) taught a method for utilizing a single linker (or more) to convert two naturally aggregated but chemically separate polypeptide chains into a single polypeptide chain which will fold into a three dimensional-structure very similar to the original structure made of two polypeptide chains. The two-chain $V_H$-$V_L$ structure can be modified by selecting an appropriate linker peptide or polypeptide sequence having a known flexible conformation that permits it to connect between C terminal region of the H chain and the N terminal region of the L chain which would normally be parts of the Fv fragment, thereby creating a polypeptide structure with a sequence comprised of the combination of the known sequence of the $V_H$ and $V_L$ domains and of the linker. This new polypeptide chain can then be manufactured with reduced risk that the chain would fail to fold successfully into the desired structure. Soluble scFv can be released from phage as approximately 25 kDa fragments (Skerra, A. et al., Biotechnology 9:273–278 (1991). As is well-known in the art, scFv polypeptides chains can be produced in bacteria, yeast cells, mammalian cells and even in plants (McCormick, A. A. et al. Proc. Nat'l. Acad. Sci. USA 96:703–708 (1999)).

Also preferred for therapeutic uses are humanized mAbs. Production and use of humanized antibodies, particularly in therapy, are reviewed in the following references: Bodey B et al. Curr Pharm Des. 2000, 6:261–276; Welt S et al. Semin Oncol. 1999, 26:683–690; Seymour L, Cancer Treat Rev. 1999, 25:301–312; Colcher D, et al. Q J Nucl Med. 1999, 43:132–139; Fan Z C, et al. J Mol Recognit. 1999, 12:19–32; Ryan A M, et al. Toxicol Pathol. 1999, 27:78–86; Goldenberg M M, Clin Ther. 1999, 21:309–318; Yoshizaki K, et al, Springer Semin Immunopathol. 1998;20:247–259; Vaswani S K, et al. Ann Allergy Asthma Immunol. 1998, 81:105–115; Halloran P F, et al. Clin Biochem. 1998, 31:353–357; Vaughan T J, et al. Nat Biotechnol. 1998, 16:535–539; Fan Z, et al. Curr Opin Oncol. 1998, 10:67–73; Harris W J, Biochem Soc Trans. 1995, 23:1035–1038; Carter P, et al. J Hematother. 1995, 4:463–470; Owens R J, et al. J Immunol Methods. 1994, 168:149–165; Pimm M V, Life Sci. 1994;55:PL45–49; Winter G, eta!. Immuunol Today. 1993, 14:243–26; Davidson J, et al. Br J Hosp Med. 1993, 49:121–122; Lewis A P, et al. Year Immunol. 1993;7: 110–118; Jolliffe L K, Int Rev Immunol. 1993;10:241–250; Parren P W, Hum Antibodies Hybridomas. 1992, 3:137–145; Wright A, et al. Crit Rev Immunol. 1992;12:125–168; Sandhu J S, Crit Rev Biotechnol. 1992;12:437–462; Mountain A, et al., Biotechnol Genet Eng Rev. 1992;10:1–142; Larrick J W, et al., Hum Antibodies Hybridomas. 1991, 2:172–189.

Frenkel D et al., J Neuroimmunol, 2000, 106:23–31 described the first isolation of a scFv that has anti-aggregating properties toward Aβ fibrils. This scFv was constructed from variable regions of Ig H and L genes of an anti-Aβ IgM mAb designated 508. MAb 508 had anti-aggregating properties and promoted disaggregation of disease Aβ fibrils, thereby preventing he Aβ's toxic effect on cultured PC-12 cells. The $V_L$ domain of the 508 (Fv) contained a Cys residue in the third complementary determining region (CDR3) at position 96 which affected its solubility and stability. Site directed mutagenesis was used to replace the Cys codon with a Phe codon, resulting in a mutant "508F(Fv)" with increased storage stability and higher affinity compared to the wild type. 508F(Fv) prevented neurotoxicity of Aβ and disrupted the fibril structure. The ability to dissolve already-formed Aβ fibrils makes this type of scFv molecule a good candidate for intracellular expression and modulation of BriPP processing in accordance with the present invention. An scFv, for example, derived from a mAb of this invention that is specific for an epitope of ABri or ADan and that can dissolve fibrils made of these mutant peptides is useful as a therapeutic protection molecule for FBD or FDD.

Inhibition of Amyloid Processing

Evidence from studies of AD suggest that the formation of amyloid plaques may play a central role in the pathogenesis. Therefore blocking amyloid formation may be an effective therapeutic strategy. The present invention is therefore directed to methods of inhibiting formation of ABri or ADan containing amyloid in subjects having or at risk for FBD or FDD, respectively. For review of approaches that are useful for inhibition of amyloid processing and inhibition of amyloid formation, which can be modified readily for use in the present invention, see Soto. C., Molec. Med. Today 1999, 5:343–350 and Lansbury, P T, Curr. Opin. Chem. Biol., 1997, 1:260–267. Several different approaches can be taken to inhibit amyloid formation from mutant ABriPP and ADanPP.

Suppression of APP expression

Selective downregulation of ABriPP or ADanPP may be an effective means to inhibit production of ABri or ADan. In an AD model, mice in which the APP gene was altered to reduce APP expression exhibited neurological disorders (Muller U, et al., Cell 1994: 79: 755–765. However, because FBD and FDD patients are heterozygous for the mutation, downregulation of the product of one of two alleles may not be similarly deleterious.

Inhibition of ABri and/or ADan Peptide Production

The similarities in phenotype of the FBD and FDD mutants (and their resemblance to AD) suggests that inhibition of the production of the respective amyloid peptides may reduce the rate of in vivo amyloid formation. The amyloid peptides can be derived from cell-surface precursor proteins. In cell culture studies of Aβ, Aβ1-42 constituted 5–10% of total secreted Aβ, which, in turn, represented a minor portion of the total APP catabolites. Aβ1-42 is detectable in cerebrospinal fluid as a minor constituent of total Aβ. Based on the notion that Aβ1-42 may be insignificant biologically albeit highly significant pathologically, selective inhibition of its production would not be expected to have adverse side effects. Thus, in this invention, inhibition of the formation of mutant ABri and/or ADan peptides from the BriPP will prevent or attenuate amyloid deposition and thereby contribute to the treatment of subject with FBD or FDD. Again, because of heterozygosity, targeting of this treatment to the mutant protein only would be expected to be even less risky.

This effect can be accomplished by directly inhibiting the protease responsible for generating the ABri and ADan peptides or by indirectly affecting BriPP processing, e.g., via a cell-surface receptor or other protein that interacts with BriPP during this reaction sequence, thereby decreasing amyloid peptide production. The latter strategy is suggested by the recent identification of the presenilin PS1 interaction with β-catenin, which may be involved in signalling pathways initiated at the cell surface (Zhou Z et al., *Neuroreport* 1997, 8:1489–1494).

Targeting the proteases is an attractive strategy that has received the most attention because protease inhibition is a well established therapeutic strategy. Since the proteases involved in BriPP processing have not been completely isolated (though see discussion of Furin, below), screening for inhibitors is preferably done in whole cell cultures. Inhibition of production amyloid protein in cell culture (and enhancement of the major-secretase pathway) using a broad spectrum serine protease inhibitor has been reported (Citron M et al., *Neuron* 1996, 17:171–179). The production of one peptide, e.g., ABri, may be selectively inhibitable by a protease inhibitor that does not affect the production of the other peptide. There may be more than one secretase activity or one secretase may tolerate a wider variety of substitutions than has been typical for proteases (Tischer E et al., J Biol Chem 1996, 271: 21914–21919).

Inhibition of the Formation of ABri or ADan Amyloid Fibrils

In contrast to APP expression and Aβ production in the setting of AD, amyloid peptide fibrillization is purely pathological, and therefore a most preferred point of therapeutic intervention in that disease. This, can of course be carried over and applied to the present disease/mutant protein context. Inhibition of protein aggregation is a known therapeutic approach. For example, inhibitors of sickle-cell hemoglobin fibrillization have been tested in the clinic and inhibitors of systemic amyloidosis have been shown to be effective in animal models (Merlini G et al., Proc Natl Acad Sci USA 1995, 92: 2959–2963; Kisilevsky R et al., Nat Med 1995, 2: 143–148).

In vitro mechanistic studies of amyloid formation suggest that nucleation and growth of amyloid fibrils occur by distinct mechanisms and thus represent distinct targets for inhibitory agents. For example, apoE inhibits the nucleation of fibrils, but not fibril growth and seeding (Gearing M et al., Ann Neurol 1996, 39: 395–399.; Evans K C et al. Proc Natl Acad Sci USA 1995, 92:763–767). An preferred therapeutic agent would have a similar mechanism of action.

Recently, a discrete metastable intermediate in the in vitro process of Aβ fibril formation has been identified and characterized by atomic force microscopy (Harper J D et al., *Chem Biol*, 1997, 4:119–125.) This study of in vitro amyloid formation (by Aβ1-40 and Aβ1-42) demonstrated the existence of a discrete, but metastable, form of Aβ aggregate (designated the Aβ protofibril) which is an assembly intermediate. The protofibril may form in a cellular compartment and could be a constituent of diffuse amyloid. See, for example, Martin BL et al., *J Biol Chem* 1995, 270:26727–26730) which reports on the processing of the Swedish mutation APP in cell culture. A significant amount of amyloid peptide that was not extractable from the medium was proposed to be intracellular. The effect of various perturbations on the secretion and production of intracellular Aβ showed that the secretory and intracellular pathways are distinct. The Aβ amyloid protofibril is a discrete species which appears rapidly, grows slowly and is then rapidly converted into "mature" fibrils that resemble those extracted from AD brains The Aβ amyloid protofibril may be the predominant form of Aβ deposit (i.e., diffuse amyloid) in asymptomatic high risk individuals (for late-onset AD). Compounds that inhibit protofibril formation and/or the protofibril-fibril transition are effective therapeutic agents in FBD or FDD.

Although a most preferred target for an FBD or FDD therapeutic would be an early intermediate such as the protofibril, it is desirable to identify compounds that could inhibit fibril growth in symptomatic individuals who already have extensive amyloid plaque deposits. An ideal therapeutic would prevent further deposition and, possibly, allow resolubilization of existing plaques, and hence ameliorate symptoms. A simple and practical assay to screen for compounds that inhibit deposition of ABri or ADan onto pre-existing plaques measures the deposition of radiolabeled amyloid peptide present at very low concentrations, onto a preformed fibrillar material. In an example of such a method (Esler W P et al., Nat Biotechnol 1997, 15: 258–263, the properties of this reaction were correlated with Aβ deposition onto brain slices containing amyloid plaques. Such an assay is used to screen compounds which affect the amount of deposition at a single time point. This assay is unlikely to identify molecules which affect the early stages of amyloid formation, that is, nucleation, protofibril growth, and protofibril-fibril transition.

The availability of simple, cell-free, high-throughput screens is a practical advantage to this strategy of inhibiting fibril formation (Wood S J et al., J Biol Chem 1996, 271: 4086–4092). Protofibril nucleation may take place in a cellular compartment in which the amyloid peptide may be concentrated to a point beyond its critical concentration. After release of the protofibril, transition to fibrils and fibril growth may occur extracellularly.

As noted above, anti-ABri or anti-ADan antibodies are also used to inhibit fibril formation and dissociate fibrils.

Suppression of Neurodegenerative Effects of ABri and ADan Amyloid Fibrils

In many reports of in vitro biological activities of Aβ, the biological activity was not associated with monomeric Aβ, and, existence of the fibrillar form of Aβ was required for activity. It is possible that a non-fibrillar aggregate which is formed concurrently with the fibril is actually the bioactive entity. Any of the reported cytotoxic activities of amyloid peptides could be targeted by high-throughput screening assays. Since it is likely that more than one such in vitro cytotoxic activity contributes to neuronal dysfunction (where studied in AD), blocking the pathogenic effects of amyloid fibrils may require several compounds. If that is the case for treating FBD or FDD, this strategy is less preferred.

Finally, Tagliavini et al. Science 1997, 276: 1119–1122, reported that compounds that have some effect in systemic amyloidosis (see Merlini et al., supra) also inhibit the transmission of scrapie in hamsters, which seems to involve amyloid formation by the prion proteins. This finding suggests that these compounds recognize shared features of all amyloids, including ABri and ADan, and are useful in the therapeutic embodiments of the present invention.

For illustrative purposes, a rough analogy has been drawn between (1) the emerging relationship between the amyloid peptide, the amyloid protofibril, neuritic amyloid plaques and disease (e.g., in the more extensively studied AD context), and (2) established relationship between cholesterol, high-density lipoprotein (HDL), atherosclerotic plaques, and heart disease.

Agents which lower plasma cholesterol levels are effective in reducing risk of heart disease. Similarly, agents which lower ABri or ADan levels or suppress amyloid fibril formation could be effective therapeutic agents against FBD or FDD. Widespread use of cholesterol-lowering agents is based on screening for individuals with high HDL levels, since that form of cholesterol is the strongest risk factor for heart disease. This screening allows high risk individuals to be identified and treated before they experience symptoms. By analogy, given the availability of an effective therapeutic, it would be optimal to identify and treat presymptomatic individuals at risk of developing these dementias. Those individuals may not have elevated amyloid peptides in plasma; therefore, a practical method to noninvasively measure something that is analogous to HDL, possibly the Aβ protofibril, in brain would be desirable. Such a method would allow rapid assessment of the efficacy of an amyloid inhibitor in clinical trials and the monitoring of drug dosage in the clinic.

Using synthetic analogs of Aβ(1–40) that contain single amino-acid substitutions, Soto and colleagues found that a transition between a random coil/α-helix structure and a β-strand conformation in the Aβ N-terminal domain modulates amyloid formation, rendering two different species of Aβ in solution: one 'able' and another one 'unable' to form amyloid (Soto C. et al.,(1995) J. Biol. Chem., 270:3063–3067; Soto C. et al., (1996) Biochem. J., 314:701–707). Therefore, a key event in amyloidogenesis may be the conversion of the normal soluble Aβ conformer into the β-sheet-rich amyloidogenic intermediate. According to the present invention, ABri or ADan amyloid formation is dependent on hydrophobic interactions among altered amyloid peptides that adopt an antiparallel β-sheet conformation.

Several, unrelated small molecules prevent amyloid fibrillogenesis or inhibit Aβ toxicity, or both, in vitro and may be useful in the setting of FBD and FDD. These include the cationic surfactant hexadecyl-N-methylpiperidinium -bromide, sulfonated dyes such as Congo red, small sulfonated anions and benzofuran-based compounds. Other molecules that may be inhibitors that can ameliorate pathology associated with ABri or ADan include rifampicin, melatonin, nicotine, estrogen and anthracycline 4'-iodo-4'-deoxydoxorubicin. None of the foregoing group of molecules are specific and most are associated with toxicity.

A preferred approach to make inhibitors of amyloid formation is to design specific peptide ligands based on the well-known self-recognition ability of the amyloid proteins and on the study of the structural requirements for amyloid protein fibrillogenesis. The central hydrophobic region of Aβ (residues 16–20) was shown to be critical for the interaction of Aβ monomers (Tjernberg L. O. et al. (1996) J. Biol. Chem., 271:8545–8548). This knowledge was used to develop a peptide that contains a sequence that binds Aβ and partially inhibits amyloid fibril formation in vitro. Binding of a synthetic peptide to the amyloid protein may not be enough to induce stable inhibition of fibrillogenesis. Rather, incorporation of a disrupting element is important in addition to the binding fragment (Ghanta J. et al., (1996) J. Biol. Chem., 271:29525–29528). A prototype inhibitor that comprised Aβ15-25 (recognition element) linked to an oligolysine fragment (disrupting element) prevented Aβ toxicity in cell culture and changed the morphology of amyloid fibrils. However, the peptide did not alter Aβ secondary structure or prevent its aggregation.

β-sheet Breaker Peptides as Inhibitors of Amyloid Formation

As described by Soto (supra) formation of amyloid is basically a problem of protein folding. A mainly random-coil soluble peptide becomes aggregated, adopting a β-pleated sheet conformation. Amyloid formation proceeds by hydrophobic interactions among conformationally altered amyloidogenic intermediates which become structurally organized into a β-sheet conformation upon peptide interaction. Hydrophobicity appears to be important for inducing the interaction of the monomers leading to aggregation, while the β-sheet conformation might determine the ordering of the aggregates into amyloid fibrils. The present approach, modeled after Soto, is to employ β-sheet breaker peptides which are short synthetic peptides homologous to ABri or ADan that bear a similar degree of hydrophobicity but a very low propensity to adopt a β-sheet conformation (Soto C et al., Biochem. Biophys. Res. Commun., 226:672–680; Soto C. et al. (1998) Nat. Med., 4:822–826). The breaker peptide should then bind specifically to ABri or ADan, to form a complex that stabilizes the physiological conformation and destabilizes the abnormal conformation.

A preferred approach is to focused on hydrophobic regions in the ABri or ADan proteins and to introduce (1) Pro residues to server as blockers of β-sheet formation and (2) charged residues at the ends to increase solubility. Proline rarely forms part of β-sheets and does not occur in the interior of antiparallel β-sheets. In studies of Aβ, introduction of Pro residues into short peptides homologous to Aβ resulted in non-amyloidogenic analogues 24.

A β-sheet breaker peptides preferably has between 5 and 11 residues, bind ABri or ADan with high affinity, inhibits peptide conformational changes that result in amyloid formation and also dissolve preformed fibrils in vitro. One can employ a animal model of amyloidosis, e.g., by intracerebral injection of ABri or ADan protein fragments and test whether co-injection of the short β-sheet breaker peptide decrease cerebral amyloid accumulation and blocks the deposition of fibrillar amyloid-like lesions in the animal brain. Soto, 1998, supra found a compound that prevented amyloid-like deposition in vivo. A β-sheet breaker peptide injected 8 d after the injection of Aβ disassembled preformed Aβ fibrils in rat brain in vivo, leading to a reduction in the size of the amyloid deposits (studies in which one of the co-inventors participated). Removal of amyloid by the β-sheet breaker reversed the associated histological changes, including neuronal shrinkage and microglial activation, suggesting that amyloid is responsible for those brain abnormalities. These peptides may be modified chemically to increase permeability at the blood-brain barrier and resistance to proteolysis in plasma without reducing its biological or pharmacological activity (Poduslo J. F. et al. (1999) J. Neurobiol., 39:371–382).

The concept of β-sheet breaker peptides provides a potentially general strategy to treat diseases caused by defective protein folding, such as amyloidosis-related disorders, and are particularly applicable to FBD and FDD.

Enzymes Involved in Processing of BriPP

Furin, a secretory pathway endoprotease, may be involved in the processing of the BRI precursor protein (Kim, S-H. et al. (1999) Nature Neurosc 2:984–988.), since the sequence KGIQKR ides (SEQ ED NO:26), located immediately before the ABri and ADan N-terminus, matches the consensus recognition sequence for proprotein convertases that belong to the subtilisin superfamily of calcium-dependent serine endoproteases (Zhou, A. et al. (1999) J. Biol. Chem. 2.74:20745–20748).

The amino-acid sequencke of BriPP that flanks the predicted cleavage site, KGIQKREA (SEQ ID NO:27), is highly reminiscent of a consensus sequence required for processing by the prohormone convertase, furin (Nakayama, K, Biochem. J. 327, 625–435 (1997); Molloy, S. S., et al., Trends Cell Biol. 9, 28–3.5 (1999)).

BriPP adopts the topology of type-II integral membrane proteins. Moreover, both wild type Bri and the ABri mutant are constitutively processed between Arg243 and Glu244 in transfected mammalian cells, leading to the production and secretion of C-terminal peptides; furin seems to be a critical factor that mediates endoproteolysis of the precursor proteins. Secretion of peptides derived from the mutant ABri precursor was enhanced compared to peptides generated from the wild type, suggesting that the C-terminal eleven amino acids in ABri effect furin-mediated proteolysis in a dominant fashion. EM studies revealed that ABri peptides assemble into irregular, short fibrils.

Thus, one therapeutic embodiment of this invention is directed to the inhibition of the enhanced furin-mediated processing of mutant ABri (or ADan) that plays a role in generating fibrillogenic peptides that may initiate pathogenesis in FBD (or FDD). This method employs a protease inhibitor that inhibits Furin or any other convertase or secretase enzyme that participates in the processing of BriPP to ABri or ADan.

Having now generally described the invention, the same will be more readily understood through reference to the following examples which are provided by way of illustration, and are not intended to be limiting of the present invention, unless specified.

EXAMPLE I

Familial British Dementia (FBD)

Using a combination of formic acid or SDS solubilization and gel filtration chromatography, the present inventors isolated amyloid fibrils from leptomeningeal and parenchymal deposits of case V41 (Plant et al., supra), a female member of this pedigree that presented with the disease symptoms at age 56 and died at age 65.

A prominent ~4 kDa component was clearly defined in SDS-polyacrylamide gels in both preparations. MALDI-TOF mass spectrometry analysis of the leptomeningeal fraction indicated the presence of a peptide having a molecular mass of 3,934.6±1 Da (referred to herein as the "4 kDa component").

Direct sequence analysis did not retrieve a primary sequence with the expected yield. However, a minor sequence SNXFAIXXFENXFAVEXL [SEQ ID NO:16], representing less than 5% of the protein loaded, was obtained in each study aimed at retrieving direct N-terminal sequence information. More reliable sequence data were acquired from internal peptides generated by trypsin digestion of the 4 kDa component and purification by microbore reverse-phase HPLC.

Three sequences were obtained from an equivalent number of HPLC peaks:

(i) HFENK [SEQ ID NO:17]

(ii) FAVETLICSR [SEQ ID NO:18], and (iii) NIIEEN [SEQ ID NO:19].

The lack of a lysine (K) or arginine (R) residue at the C-terminus of the latter peptide suggested that this fragment comprised the C-terminus of the molecule.

Homology searches in protein databanks retrieved no matching sequences. However, the search of expressed sequence-tag (EST) sequence databanks using the BLAST algorithm (on the World Wide Web at ncbi.nlm.nih.gov/BLAST) uncovered ESTs showing almost perfect matches with the amyloid fragments.

These findings not only revealed the order of the peptides in the sequence of this amyloid protein, but also indicated the presence of an arginine residue at the C-terminus of peptide FAVETLICSR [SEQ ID NO:18] that could not be found in any of the EST clones. In fact at that position, the EST clones always featured a stop codon.

In addition, the peptide NIIEEN [SEQ ID NO:19] has the sequence that would be encoded by a 3'-untranslated segment located after the stop codon and immediately before a second stop codon.

Since analysis of the EST sequences clearly indicated that this amyloid protein was a fragment derived from a much larger precursor molecule, the present inventors proceeded to clone and sequence the corresponding cDNA.

EXAMPLE II

Nucleotide Sequence of FBD-associated Amyloid Peptides

The complete nucleotide sequence of a ~1.8 kb human transcript was obtained from the consensus of independent cDNA clones recovered by standard 5' and 3' RACE using Marathon®-ready cDNA from kidney and brain cDNA libraries (Clontech, CA), EST clones AA149631, AA149499, R76391 and R86131, and clone THC212690 (TIGR gene index database; on the World Wide Web at tgr.org. EST clones AA149631 and AA149499 containing the full-length cDNA were obtained from ATCC (Rockville, Md.) and completely sequenced. The longest open reading frame (ORF) predicted a protein of 266 amino acids.

As indicated in Table 1, the first ATG is located 150 bp downstream of an in-frame TAG stop codon, and has a classical Kozak consensus sequence (CGCC<u>ATG</u>G) (Kozak, M. Nucleic Acids Res. 15:8125–8148 (1987)).

The amino acid composition of the 266-residues ABri precursor protein is shown below, where the number of residues of each amino acid are shown.

| Ala | 22 | Gly | 10 | Met | 5  | Ser | 9  |
| --- | -- | --- | -- | --- | -- | --- | -- |
| Cys | 9  | His | 6  | Asn | 12 | Thr | 9  |
| Asp | 19 | Ile | 24 | Pro | 15 | Val | 18 |
| Glu | 21 | Lys | 19 | Gln | 7  | Trp | 2  |
| Phe | 13 | Leu | 24 | Arg | 9  | Tyr | 13 |

This information yields a calculated Mr of 30,329.05 and a pI of 4.86.

Therefore, the coding sequence of the precursor molecule starts at nucleotide 170, producing a protein of 266 amino acids with a calculated Mr of 30,329.05 Da and a theoretical pI of 4.86. It contains 9 cysteine residues and is highly rich in leucine (9.02%) and isoleucine (9.02%). Hydropathy analysis of the predicted precursor protein sequence, calculated according to Kyte & Doolittle (*J.Mol.Biol.* 157:105–132 (1982)) and Sonnhammer et al. (ISMB98 :175–182 (1998)) algorithms indicated the presence of a putative single transmembrane spanning domain at positions 52–74, suggesting that the molecule is a type II integral transmembrane protein with an extracellular C-terminal domain (Tables 1, 2, 4; FIG. 1A//1B). A single potential N-glycosylation site was identified at asparagine 170.

No evidence existed for either a signal sequence for transport through the endoplasmic reticulum membrane or for distinct motifs of known protein families.

Homology searches performed with the sequences retrieved for the human cDNA showed that ESTs of chicken, rat, mouse, rabbit and pig origin had been deposited in the databanks, as their ORFs were highly homologous to the human sequence (i.e., identity between human and mouse is 96%). Studies on the mouse homologue suggested that the protein may be a member of a multi-gene family (Deleersnijder, W et al. *J.Biol.Chem.* 271:19475–19482 (1996)).

The gene encoding the BRI transcript was mapped to human chromosome 13 by fluorescence in-situ hybridization (FISH) analysis. Further confirmation was obtained by analysis of positive matches (G25377 and G28192) retrieved. from sequence tagged sites (STS) databases.

Hybridization of the human precursor protein clone to Northern blots identified a major mRNA transcript of ~2.0 kb and a second transcript of ~1.6 kb, which were expressed in most regions of the human brain as well as in several peripheral tissues (FIG. 2). Highest expression was observed in brain, placenta, kidney and pancreas whereas lower expression levels were observed in heart, lung, liver and skeletal muscle. Northern analysis of different brain regions detected predominantly the 2.0 kb transcript in cerebellum, subthalamic nucleus, substantia nigra and hippocampus, while lower expression levels were observed in the spinal cord, caudate nucleus and corpus callosum.

All cDNA clones that include both 5' and 3'-UTRs recovered so far have a size in the range of the signals observed in Northern hybridizations, indicating that both transcripts may represent either alternatively spliced or polyadenylated isoforms. As indicated in Table 1, the 3' region of the precursor protein contains 5 polyadenylation signals.

Transcripts using the first polyadenylation signal ATTAAA were found in ESTs from placenta (AI189911, AI200443, R76391), fetal liver/spleen (AI248856, AI023889, H73884), aorta (D58336, D57790, D57728, D57976), white blood cells (AH356254), parathyroid tumors (AI075223, AI168126), pregnant uterus (AA135881) and fetal heart (W67150).

Transcripts that used the second polyadenylation signal TATAAA were found in breast (R86131), pregnant uterus (AA149499), pancreas (AA113057), cerebellum (AA323476, AA325464), parathyroid tumor (W56225), placenta (N40489) and heart (C04137). Two perfect polyadenylation signals AATAAA are followed by a fifth poly-A signal ATTAAA, all reported in various ESTs (THC212690) derived from placenta, liver/spleen, heart, parathyroid tumors, pregnant uterus, pancreas, cerebellum, fibroblasts, white blood cells, colon, testis, lung, epididymis, kidney, fetal heart, fetal liver/spleen, trabecular bone cells, senescent fibroblasts and infant brain.

Nucleotide sequence analysis of the transcript isolated from seven affected members of the FBD family revealed a single nucleotide substitution in the stop codon, mutating TGA to AGA at codon 267. This introduces an arginine residue and results in a longer ORF of 277 amino acids instead of 266 (Table 2 and FIG. 1B).

The arginine residue at the C-terminal end of peptide FAVETLICSR (SEQ ID NO:18) was confirmed by amino acid sequence analysis; the peptide NIIEEN (SEQ ID NO:19) exhibited perfect homology with a 3'-untranslated segment located after the stop codon 267 and immediately before the next in-frame stop codon at position 278 (indicated in bold). According to mass spectrometric analysis and the sequence data, the ABri amyloid sequence is encoded by the last 102 nucleotides of the mutated precursor. The XbaI restriction site introduced by the mutation at nucleotide 799 (codon 267) is underlined.

The mutation was not found in unaffected individuals (n=7) of the same kindred. The change of a stop codon TGA into an arginine codon AGA also created a XbaI restriction site that was detectable by digesting PCR-amplified genomic DNA with this restriction endonuclease.

As indicated in FIG. 3, the 191 bp amplification product remained undegraded in wild-type sequences, whereas in mutant sequences, the PCR product was cleaved into a 75 and a 116-bp fragments.

Affected members (filled symbols) and at-risk members (hatched symbols) tested so far proved to be heterozygous, carrying only one allele with the XbaI site (some examples are shown in FIG. 3). These results were confirmed by DNA sequencing after cloning of the amplified fragments into pCR2.1 vector (Invitrogen, CA).

Methods

Amplification of genomic DNA samples isolated from peripheral blood leukocytes of living family members and autopsy tissue from case IIB(4) was performed using oligonucleotide primer pairs F: 5'CGTGAAGCCAGCAATTGTTTCGCA-3' [SEQ ID NO:20]; and

R: 5'-AGCCCTGTTTGCTACTTACATG-3' [SEQ ID NO:21]

(product=191 bp) by PCR using 250 μmol dNTPs, 2,5 mM MgCl2, 50 pmol oligonucleotides, in 100 μl, cycled for 30 cycles of 94° C. for 30 s, 50° C. for 30 s, 72° C. for 30 s. PCR products were cloned and sequenced by automated cycle sequencing (ABI, Foster City, Calif.). Restriction enzyme analysis of the amplified PCR products was performed with XbaI (Gibco, BRL) according to the manufacturer's protocol, and the resulting products were resolved by non-denaturing polyacrylamide gel electrophoresis. M indicates φ174 RF DNA Hae III fragments marker. In wild-type sequences, no cleavage was observed, whereas in mutant sequences the PCR product was cleaved into 75 and 116-bp fragments. Affected members (filled symbols) and at-risk members (hatched symbols) carried one allele with the XbaI site. The XbaI site was not present in all obligate escapees (open symbol with E) and all normal controls The next in-frame stop codon was found at codon 278 (TAA), resulting in an ORF of 277 residues. Thus with the mutant precursor molecule extended 33 nucleotides at the C-terminus.

This nucleotide substitution segregated with the disease, and was not found in asymptomatic family members, individuals with unrelated neurologic disorders (n=28) or healthy controls (n=39) of comparable ethnic origin.

Because the altered stop codon in the British family is conserved in the homologous murine sequence, it was concluded that this nucleotide substitution was a pathogenic mutation rather than an innocent polymorphism.

Antibodies

The purified 4 kDa amyloid peptide as well as a synthetic peptide comprising the last 10 residues of the ABri sequence were used as antigens to raise polyclonal antibodies in rabbits.

Method

The 4 kDa purified ABri amyloid as well as a synthetic peptide CTVKKNIIEEN (SEQ ID NO:11; see above), homologous to the 10 C-terminal residues of the ABri molecule and containing an extra N-terminal cysteine for coupling to the immunogenic protein carrier, keyhole limpet hemocyanin, were used to induce a polyclonal antibody response in rabbits. After an initial immunization with 200 μg of antigen emulsified in RIBI adjuvant, animals were boosted with 50 μg of antigen every three weeks for twelve weeks. Specific antibodies were tested by ELISA and dot blot analysis against a synthetic peptide homologous to the full length ABri sequence. The IgG fraction was purified from the rabbit serum by specific binding to protein G (Gammabind G, Pharmacia). Temporal adjacent sections of case V41 (Plant et al., supra) were immunostained with both antibodies followed by biotinylated anti-rabbit IgG and streptavidin-HRP. Color was developed with diaminobezidine and hydrogen peroxide.

Parenchymal plaques were stained with Ab 547 (anti-Bri amyloid; 1:300) and Ab 338 (anti-C-terminal synthetic peptide; 1:1,000), respectively. Leptomeningeal vessels were stained with Ab 338. No immunoreactivity was seen after absorption of Ab 547 and 338 with full length ABri peptide (100 μg of peptide per 50 μl of antibody) for 1 hour at 37° C. and 16 hours at 4° C. followed by centrifugation at 14,000×g for 5 minutes. The presence of amyloid deposits was corroborated in parallel sections by Congo red staining. No immunoreactivity was observed using Abs 547 and 338 in brain sections of a number of other hereditary diseases affecting brain or involving amyloid deposition elsewhere in the body. Paraffin sections counterstained with hematoxylin were viewed at magnifications of 100× or 40×.

Results

As shown by immunohistochemistry, antibodies made against both purified and synthetic amyloid peptides specifically recognized amyloid deposits.

Parenchymal plaques stained with antibodies 547 (anti-Bri amyloid; 1:300) and 338 (anti-C-terminal synthetic peptide; 1:1,000), respectively. Perivascular plaque immunoreactivity with Abs 547 and 338, respectively, was evident. Leptomeningeal vessels were stained with 338 Ab.

The specificity of the immunostaining was corroborated by absorption of both antibodies with a synthetic peptide homologous to the 34-amino acid full-length ABri amyloid. The immunoreactivity co-localized with yellow-green birefringent material observed under polarized light after Congo red staining. In many instances, the presence of Congo red negative diffuse plaques was revealed by immunoreactivity with the antibodies. Leptomeningeal vessels full of amyloid were clearly detected by the antibody 338. Identical results were obtained with antibody 547.

Anti-ABri amyloid (antibody 547) recognized the same type of lesions that were detected by the antibody against the synthetic C terminal peptide ABri (antibody 338), although the latter exhibited stronger immunoreactivity. As noted earlier, no immunoreactivity was observed using these antibodies in brain sections of a number of other hereditary diseases affecting brain or involving amyloid deposition elsewhere in the body. The diseases examined were sporadic CAA; sporadic AD; Down's syndrome; hereditary cerebral hemorrhage with amyloidosis-Dutch type; hereditary cerebral hemorrhage with amyloidosis-Icelandic type, Hungarian transthyretin cerebral amyloidosis, and systemic cases of light chain amyloidosis (kidney), light chain deposition disease (kidney) and amyloid A (heart).

Discussion

Examples of stop codon mutations are abundant in the literature, and the most common finding is the appearance of a stop codon within the coding sequence that results in a truncated protein. It is more unusual to find mutation of a stop codon to one encoding an amino acid residue such that a longer ORF results that encodes an amino acid sequence extending up to the next in-frame stop codon. The best known examples of this type of mutation are the mutants in the globin chains of hemoglobin that are related to thalassemia. To the present inventors' knowledge, this was the first example of a point mutation in a stop codon that resulted in a longer molecule whose C-terminal segment is released and found deposited as fibrillar amyloid in the brain of a genetically determined dementia patient.

EXAMPLE III

Familial Danish Dementia

The present inventors purified amyloid fibrils from leptomeningeal vessels of a patient affected by FDD. The amyloid protein (termed "ADan") has a molecular mass of ~4 kDa and was blocked at the N-terminus.

From the amyloid preparation, amino acid sequence was obtained starting at position 3 of the ABri peptide (the peptide deposited in FBD, above). Analysis of the ABri gene from genomic DNA isolated from the FDD patient, indicated the presence of a ten nucleotide insertion (TTTAATTTGT; SEQ ID NO:28) between codons 265 and 266 (FIG. 1B, FIG. 5)) of the ABri precursor gene (encoding the BriPP). This insertion changes the reading frame of the ABri precursor protein up until the next in-frame stop codon at position 278.

PCR amplification was done using the following oligonucleotides (1) forward F: 5'-CGT GAA GCC AGC AAT TGT TTC GCA-3' [SEQ ID NO:22]; and (2) reverse R: 5'-ACA AAA TGT AAA GGG TGG G-3' [SEQ ID NO:23].

Results showed the presence of two amplification products. One was a 141 bp polynucleotide corresponding to the wild-type sequence, and the second was a 151 bp polynucleotide corresponding to the mutant sequence (FIG. 2).

Thus, the amyloid deposited in patients with FBD and FDD originates from the same precursor protein, carrying different genetic defects. This is illustrated in FIG. 3. In FBD, a point mutation changes the normal stop codon into an arginine, with extension of the protein by 11 amino acids at the C-terminus. FDD was characterized by a ten nucleotide duplication of the DNA sequence inserted after codon 265 and before codon 266. This insertion extends the protein by 12 amino acids at the C-terminus, with the loss of the wild type serine at the C-terminus (FIG. 3). In both FBD and FDD, the amyloid sequences (ABri and ADan) are composed, respectively, of 23 or 22 amino acids present in the wild-type sequence and 11 or 12 amino acids attributable to the genetic defects.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. An antibody specific for an epitope of mutant amyloid precursor protein ABriPP which protein has the amino acid sequence SEQ ID NO:4, or specific for its peptide fragment ABri having the sequence corresponding to residues 244–277 of SEQ ID NO:4, which epitope is not present in wild-type BriPP having an amino acid sequence SEQ ID NO:2.

2. The antibody of claim 1 that is a monoclonal antibody.

3. An immunoassay to detect the presence of a mutant precursor protein ABriPP or a mutant ABri peptide in a sample, comprising:
 (a) incubating said sample with the antibody of claim 1 or 2;
 (b) assaying the binding of said antibody to a protein or peptide in said sample, wherein binding of said antibody to said sample is indicative of the presence of said mutant protein or peptide.

* * * * *